US012134702B2

(12) United States Patent
Yum et al.

(10) Patent No.: US 12,134,702 B2
(45) Date of Patent: Nov. 5, 2024

(54) COMPOSITIONS AND METHODS FOR EXTRUSION-BASED 3D PRINTING OF SOFT MATERIALS

(71) Applicant: Board of Regents, The University of Texas System, Austin, TX (US)

(72) Inventors: Kyungsuk Yum, Fort Worth, TX (US); Amirali Nojoomi, Arlington, TX (US); Hakan Arslan, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 342 days.

(21) Appl. No.: 17/017,907

(22) Filed: Sep. 11, 2020

(65) Prior Publication Data

US 2021/0071018 A1 Mar. 11, 2021

Related U.S. Application Data

(60) Provisional application No. 62/898,951, filed on Sep. 11, 2019.

(51) Int. Cl.
*B29C 64/129* (2017.01)
*A61L 27/38* (2006.01)
(Continued)

(52) U.S. Cl.
CPC ............ *C09D 11/102* (2013.01); *A61L 27/38* (2013.01); *B29C 64/129* (2017.08); *B33Y 10/00* (2014.12);
(Continued)

(58) Field of Classification Search
CPC ..... C09D 11/102; C09D 11/101; C09D 11/38; A61L 27/38; A61L 2430/30;
(Continued)

(56) References Cited

U.S. PATENT DOCUMENTS

| 11,530,299 | B2 * | 12/2022 | Luo .................. A61L 27/52 |
| 2002/0192289 | A1 * | 12/2002 | Zheng .................. A61K 31/74 |
| | | | 604/20 |

(Continued)

FOREIGN PATENT DOCUMENTS

| CN | 104983722 | * 10/2015 | ............ B29C 64/00 |
| EP | 3563881 | * 6/2019 | ............ B29C 64/00 |

*Primary Examiner* — Nahida Sultana
(74) *Attorney, Agent, or Firm* — Thomas | Horstemeyer, LLP

(57) ABSTRACT

In accordance with the purpose(s) of the present disclosure, as embodied and broadly described herein, the disclosure, in one aspect, relates to gel-phase inks suitable for extrusion-based 3D printing and methods of making the same, as well as anisotropic hydrogels printed from the same. In another aspect, the disclosure relates to linear contractile elements constructed from the anisotropic hydrogels and 3D structures with programmed morphologies and motions comprising the linear contractile elements. In still another aspect, the disclosure relates to a process for preparing soft materials and a method to create 3D structures starting from the gel-phase inks disclosed herein. This abstract is intended as a scanning tool for purposes of searching in the particular art and is not intended to be limiting of the present disclosure.

15 Claims, 18 Drawing Sheets

(51) Int. Cl.
  *B33Y 10/00* (2015.01)
  *B33Y 70/00* (2020.01)
  *C09D 11/101* (2014.01)
  *C09D 11/102* (2014.01)
  *B29K 105/00* (2006.01)

(52) U.S. Cl.
  CPC ............ *B33Y 70/00* (2014.12); *C09D 11/101* (2013.01); *A61L 2430/30* (2013.01); *B29K 2105/0002* (2013.01); *B29K 2105/0061* (2013.01)

(58) Field of Classification Search
  CPC ... A61L 2430/40; A61L 27/52; B29C 64/129; B29C 64/106; B33Y 10/00; B33Y 70/00; B33Y 80/00; B29K 2105/0002; B29K 2105/0061
  See application file for complete search history.

(56) References Cited

U.S. PATENT DOCUMENTS

| | | | |
|---|---|---|---|
| 2013/0084449 A1* | 4/2013 | Lewis | A61L 27/56 428/221 |
| 2017/0130192 A1* | 5/2017 | Retting | C12N 5/0697 |
| 2019/0290803 A1* | 9/2019 | Bharti | C12N 5/0621 |
| 2021/0022867 A1* | 1/2021 | Shimko | B29C 64/393 |
| 2021/0071018 A1* | 3/2021 | Yum | B33Y 70/00 |
| 2021/0395558 A1* | 12/2021 | D'Andola | C09D 11/101 |

\* cited by examiner

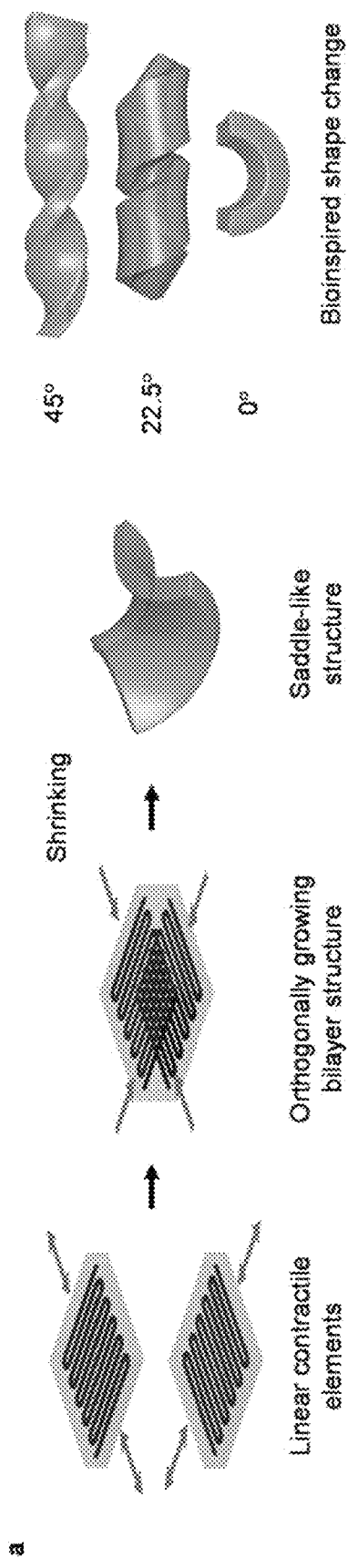
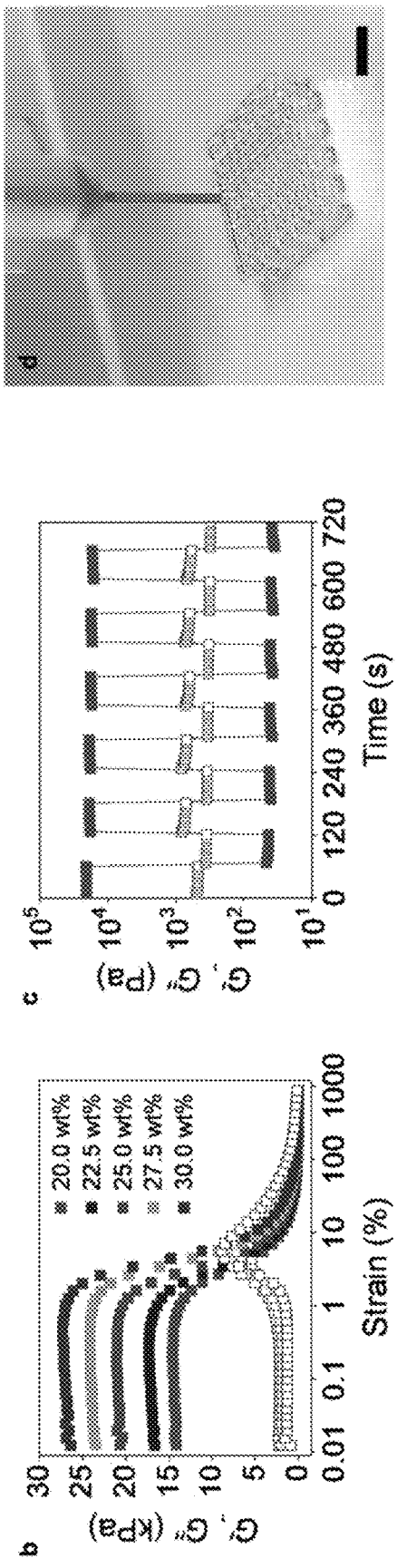
FIGs. 1a-1d

COMPOSITIONS AND METHODS FOR EXTRUSION-BASED 3D PRINTING OF SOFT MATERIALS

CROSS REFERENCE TO RELATED APPLICATIONS

This application claims the benefit of U.S. Provisional Application No. 62/898,951, filed on Sep. 11, 2019, which is incorporated herein by reference in its entirety.

STATEMENT REGARDING FEDERALLY SPONSORED RESEARCH OR DEVELOPMENT

This invention was made with government support CMMI-1636288 awarded by the National Science Foundation. The government has certain rights in the invention.

BACKGROUND

Nature has evolved a variety of soft materials that change their shapes and properties in response to internal signals or environmental cues. Inspired by such materials, researchers have developed stimuli-responsive, self-shaping materials using shape-memory polymers, liquid crystalline polymers, and hydrogels. Among these materials, hydrogels are promising for bioinspired and biomedical applications, such as soft robotics, artificial muscles, and smart medicine, owing to their physical properties, which are similar to those of biological soft tissues. Such biomimetic properties include soft polymer structures with high water content, biocompatibility, and reversible volume changes in response to external stimuli, such as temperature, light, pH, chemicals, and biomolecules. However, most synthetic hydrogels are structurally isotropic and thus show isotropic material properties and actuation. In contrast, biological tissues adopt anisotropic structures with hierarchical architectures and thus display anisotropic properties and actuation in their fundamental units. For example, muscle tissues use anisotropic microstructures, from actin and myosin in sarcomeres to muscle fibers, to generate macroscopic linear contractions. Plants produce motion through the anisotropic swelling and shrinkage of sclerenchyma tissues in response to environmental stimuli, such as humidity, touch, and light.

This anisotropy plays a critical role in shape changes and movements of biological organisms. They often achieve complex motions through the spatial arrangement of simple linear contractile elements, rather than relying on specifically designed actuators with complex structures such as those often used in man-made machines. For example, the heart generates twisting and compressive motions through the helical and circumferential arrangement of the outer two muscle layers. Plants have evolved mechanisms that convert the anisotropic swelling and shrinking of tissues into various motions, including bending, coiling, and twisting. Inspired by such mechanisms, researchers have prepared linearly-actuating anisotropic hydrogels and have combined these into bilayer structures to create various bioinspired 3D structures. Linear anisotropic behaviors have been achieved, for example, by controlling the orientation of stiff reinforcing elements in a hydrogel matrix using magnetic fields and flow-induced shear forces during 3D printing. However, these approaches need to couple fabrication processes (e.g., crosslinking of hydrogels and printing of filaments) with reinforcement alignment, limiting achievable 3D architectures. For example, the approach using magnetic fields involves multiple steps, such as rotating a magnetic field, addition of a precursor solution for each layer, and manual cutting. In addition, although previous studies have demonstrated reversible shape changes, they have mainly focused on the hydration-driven formation of 3D shapes (rather than their stimuli-responsive motions). A strategy that can directly implement linear contractile elements into 3D architectures could provide a simple yet versatile way to program various motions into 3D structures. 3D printing has great potential in this regard, but printing self-supporting 3D structures of hydrogels, including those of stimuli-responsive hydrogels, has not been fully achieved.

Shape-morphing materials have applications in various fields, such as soft robotics, programmable matter, bioinspired engineering, and biomimetic manufacturing. Certain existing approaches use swellable hydrogel structures, shape-memory polymers, and liquid crystalline elastomers with fabrication methods such as photo-patterning, self-folding and 3D printing. Although these approaches have been used to build self-shaping 3D structures with various geometries, reproducing complex 3D morphologies of living organisms, let alone their movements, has not been achieved. As an initial matter, there is still a scarcity of self-supporting, stimuli-responsive hydrogels having programmable, anisotropic linear motion capabilities. These needs and other needs are satisfied by the present disclosure.

SUMMARY

In accordance with the purpose(s) of the present disclosure, as embodied and broadly described herein, the disclosure, in one aspect, relates to gel-phase inks suitable for extrusion-based 3D printing and methods of making the same, as well as anisotropic hydrogels printed from the same. In another aspect, the disclosure relates to linear contractile elements constructed from the anisotropic hydrogels and 3D structures with programmed morphologies and motions comprising the linear contractile elements. In still another aspect, the disclosure relates to a process for preparing soft materials and a method to create 3D structures starting from the gel-phase inks disclosed herein.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1a-1k show 3D printing of orthogonally growing bilayer structures of hydrogels with programmed motions. 1a Schematic illustrating the 3D printing-based process to create 3D structures with programmed motions using a bilayer structure of orthogonally oriented linear contractile elements. The arrows indicate the direction of anisotropic actuation, perpendicular to the poly(ethylene glycol) (PEG) reinforcement direction. The angles θ shown in the legend (right figures) indicate the angle between the long axis of a bilayer structure and the direction of intrinsic curvature. 1b G' and G" of poly(N-isopropylacrylamide) (PNIPAM) inks (10 wt % N-isopropylacrylamide (NIPAM) and 1 wt % poly(ethylene glycol) diacrylate (PEGDA)) with different concentrations of the fugitive carrier (20-30 wt % as shown in the legend) on oscillatory strain sweeps (0.01-1000%) at a frequency of 1 Hz. 1c Step-strain measurement of a PNIPAM ink (10 wt % NIPAM, 1 wt % PEGDA, and 25 wt % fugitive carrier) with oscillatory strain steps between 0.5% and 250% at a frequency of 10 Hz. 1d 3D printing of a multilayer lattice structure using a 200 μm nozzle. Scale bar is 2 mm. 1e Temperature-responsive reversible volume change of a PNIPAM structure. Scale bar is 5 mm. 1f-h Optical microscope images (top view) of an as-printed 3D structure 1f and the structure at the swelled state (25° C.) 1g and the shrunk state (40° C.) 1h. Scale bar is 500 μm for 1f-h. 1i Areal swelling (black) and shrinking (red) ratios ($A_T/A_0$) of 3D structures of PNIPAM printed with different concentrations of the fugitive carrier. $A_T$ and $A_0$ are the areas of the top surface of the structures at temperature T and as-printed structures, respectively. $T_c$ is the volume phase transition temperature of PNIPAM (~32.5° C.). 1j G' and G" of DM (10 wt N,N-dimethylacrylamide (DMA) and 1 wt PEGDA), PD (11 wt PEGDA), and NA+B (10 wt NIPAM and 1 wt N,N'-methylene bisacrylamide (BIS)) inks on oscillatory strain sweeps (0.01-1000%) at a frequency of 1 Hz. 1k Areal swelling (black) and shrinking (red) ratios of the inks. NA represents the PNIPAM ink (10 wt NIPAM and 1 wt PEGDA).

Figures 1E, 1F, 1G, 1H, 1I, 1J, 1K:
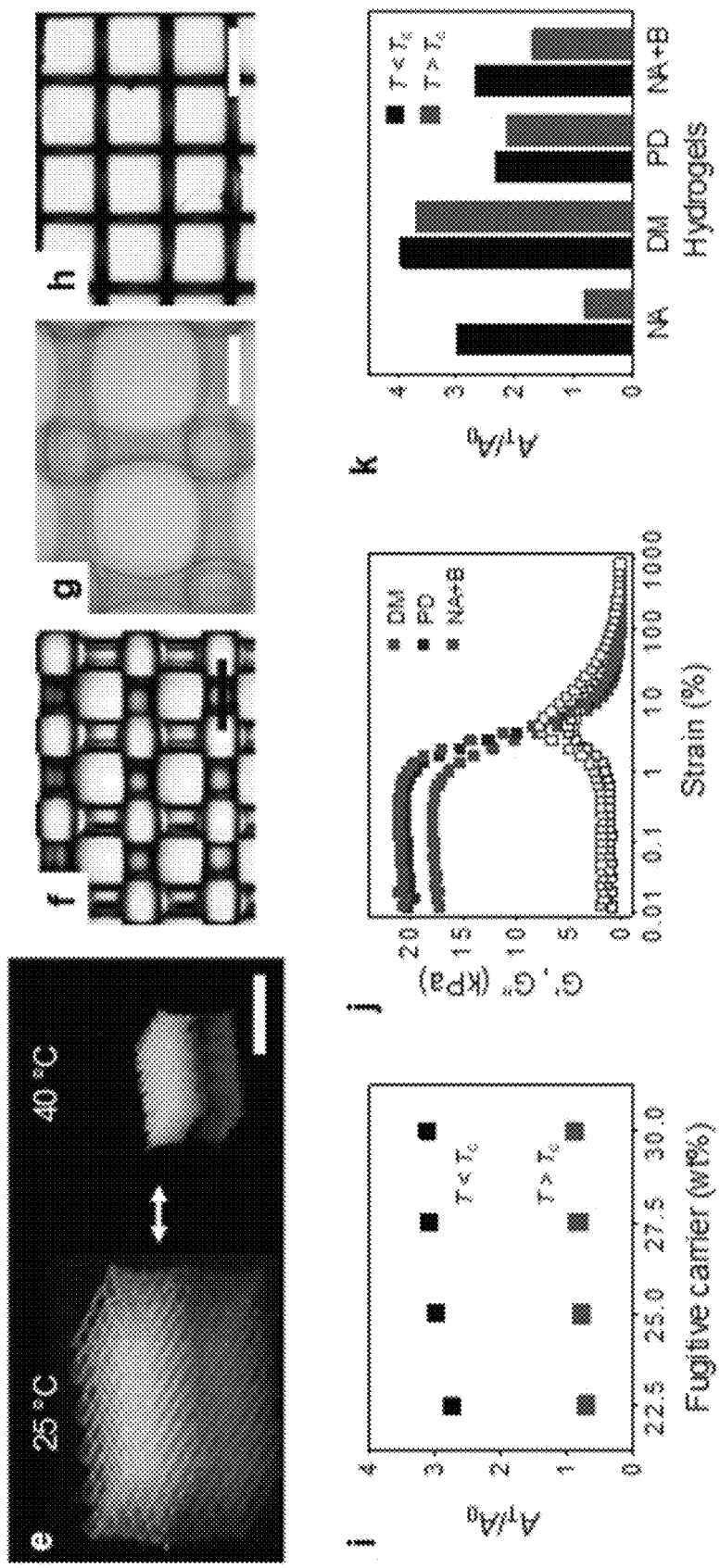

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a crosslinkable monomer," "a crosslinkable polymer," or "a crosslinker," including, but not limited to, combinations of two or more such crosslinkable monomers, crosslinkable polymers, or crosslinkers, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of an initiator refers to an amount that is sufficient to achieve the desired improvement in the property modulated by the formulation component, e.g. initiating a radical polymerization of monomers in the compositions disclosed herein. The specific level in terms of wt % in a composition required as an effective amount will depend upon a variety of factors including the amount and type of monomer, amount and type of crosslinker, amount and type of fugitive carrier, and end use of the article made using the composition.

As used herein, the terms "optional" or "optionally" means that the subsequently described event or circumstance can or cannot occur, and that the description includes instances where said event or circumstance occurs and instances where it does not.

As used herein, a "poloxamer" is a triblock copolymer with a central polypropylene oxide chain and two flanking polyethylene oxide chains. A poloxamer is nonionic; the polypropylene oxide core is hydrophobic, while the polyethylene oxide chains are hydrophilic. Poloxamers can be customized, for example, by varying the length of the polymer blocks, and different poloxamers have slightly different properties. In solution, poloxamers may exhibit temperature-dependent self-assembly and/or gelling behavior.

"Critical micelle concentration" or CMC, as used herein, refers to a concentration of an element such as a surfactant or a poloxamer above which aggregation of individual units occurs in order to minimize exposure of hydrophobic blocks or elements to a solvent such as water. CMC can vary based on atmospheric pressure, temperature, and concentration of electrolytes. Micelles typically have hydrophilic elements (such as, for example, polyethylene oxide chains) exposed at their surfaces and hydrophobic elements (such as, for example, polypropylene oxide cores of poloxamers) buried inside the micelles.

"Fugitive" as used herein refers to a compound or composition that is required for the printing processes disclosed herein but that does not appear in the final structures. For example, the compositions disclosed herein employ a fugitive carrier. This carrier has properties (e.g., shear-thinning properties) that are required for the 3D printing process but that are not needed or not wanted in the final materials. A fugitive material can be removed by various methods once the construction of printed soft materials disclosed herein is complete, including, for example, dissolution or immersion in water.

As used herein, "soft materials" refer to materials that can be deformed by thermal, mechanical, or other stresses at or near room temperature. Soft materials include, but are not limited to, biological materials, liquids, liquid crystals, granular materials, polymers, foams, gels, hydrogels, colloids, and mixtures thereof. In one aspect, provided herein are 3D printed soft materials and methods of making thereof.

"Hydrogels" as referred to herein are natural and/or synthetic crosslinked polymer networks. Hydrogels are insoluble in water and able to survive in solutions containing 90% or more water due to the crosslinking, which creates a three-dimensional structure. Hydrogels typically possess some properties similar to solids (for example, hydrogels do not flow in the same manner as fluids) and some properties similar to liquids (for example, a small molecule can diffuse through a hydrogel). A typical hydrogel will encompass a much greater mass of water than it will of polymer.

As used herein, the "storage modulus" or "elastic modulus" (represented by G' and typically assigned units in Pa) is a value representing the elastic portion of viscoelastic behavior and can be used as an approximation describing the solid-state behavior of the hydrogels disclosed herein. In one aspect, G' represents stored deformation energy of the hydrogels. Meanwhile, the "loss modulus" or "viscous modulus" (represented by G" and also typically assigned units in Pa) is a value representing the viscous portion of viscoelastic behavior and can be used as an approximation describing the liquid-state behavior of the samples disclosed herein. In one aspect, G" represents deformation energy dissipated through internal friction when flowing. In some aspects, hydrogels with G'>G" typically have a high number of internal connections (e.g., chemical bonds, physical interactions).

As used herein, "isotropic" materials possess the same properties in all directions. Meanwhile, "anisotropic" materials have properties that vary according to orientation or that are direction-dependent. In biological systems (organisms), tissues and their properties are typically anisotropic.

"Stimuli-responsive" or "stimulus-responsive" refers to a material that changes a property in response to a change in environment such as, for example, exposure to a chemical agent, visible and/or UV-irradiation, pH, temperature, ionic strength of solution, pressure, electrical potential, mechanical stress, radiation, solvent composition, and the like. In some cases, "stimuli-responsive" materials are also referred to as "smart" materials. In some aspects, hydrogels can be used to construct stimuli-responsive or smart materials. In one aspect, the materials disclosed herein exhibit temperature-responsive volume changes (see FIG. 1e).

A "linear hydrogel actuator" as used herein is an actuator (i.e., an element that causes a machine, system, or device to operate) that achieves movement in a linear fashion through swelling of the hydrogel material it is constructed from. In one aspect, linear hydrogel actuators serve as building blocks of the anisotropic hydrogels disclosed herein. In some aspects, linear hydrogel actuators as disclosed herein may be referred to or used interchangeably with the phrase "linear contractile elements." In one aspect, the linear hydrogel actuators disclosed herein can perform motions similar to or inspired by biological tissues, cells, proteins, or other structural elements. In one aspect, areal swelling and shrinking can be controlled based on choosing a temperature for the hydrogel environment that is higher or lower than the volume phase transition temperature of the polymeric structure (FIG. 1k).

As used herein, the term "alkyl group" as used herein is a branched or unbranched saturated hydrocarbon group of 1 to 10 carbon atoms, such as methyl, ethyl, n-propyl, isopropyl, n-butyl, isobutyl, t-butyl, pentyl, hexyl, heptyl, octyl, decyl, and the like.

As used herein, the term "polymer" as used herein may refer to a homo-polymer, a copolymer, a tri-polymer and other multi-polymer, or a mixture thereof.

As used herein, the term "admixing" is defined as mixing two or more components together so that there is no chemical reaction or physical interaction. The term "admixing" also includes the chemical reaction or physical interaction between the two or more components.

Unless otherwise specified, temperatures referred to herein are based on atmospheric pressure (i.e. one atmosphere).

Gel-Phase Inks

In one aspect, disclosed herein are gel-phase inks having (a) a precursor solution and (b) a fugitive carrier with shear-thinning properties. Further in this aspect, the gel-phase inks are suitable for extrusion-based 3D printing.

Precursor Solution

In a further aspect, the precursor solution can include crosslinkable monomers and/or crosslinkers; crosslinkable polymers and/or crosslinkers; biological cells with crosslinkable monomers, polymers, and/or crosslinkers; and other similar materials.

In one aspect, the crosslinkable monomers when polymerized produce stimuli-responsive polymers. In another aspect, the crosslinkable polymers are stimuli-responsive polymers. Examples of stimuli-responsive polymers include, but are not limited to, thermoresponsive polymers, light-responsive polymers, ultrasound-responsive polymers, water-responsive polymers, biodegradable polymer, pH-responsive polymers, and combinations thereof.

Stimuli-responsive polymer may respond to changes in the environment. Such changes in the environment can induce small to large changes in the stimuli-responsive polymer's properties. Upon responding to at least one stimulus, a stimuli-responsive polymer can, e.g., change shape, color or transparency, become conductive, or become permeable to water. In an exemplary embodiment, a polymer of the disclosure is one that changes its shape in response to at least one stimulus such as temperature. More preferably, a polymer herein transforms from a temporary shape (e.g., that of a liquid or solution) to a permanent shape (e.g., that of a solid). In some embodiments, a polymer herein transforms from a soft to a hard material, or from an elastic to rigid material.

In one aspect, the crosslinkable monomer possesses an olefinic group capable of undergoing polymerization such as, for example, free radical polymerization. Examples of such olefinic groups include, but are not limited to, vinyl groups, acryloyl groups, methacryloyl groups, or a combination thereof.

In one aspect, the crosslinkable monomers and polymers in the precursor composition can include thermoresponsive materials. In one aspect, the thermoresponsive polymer is partly composed of one or more monomers including, but not limited to, 4-pentenoic acid, methacrylamide, vinylphenylboronic acid, acrylamide, N-isopropylmethacrylamide, butyl acrylate, N-vinyl-2-pyrrolidinone, N-hydroxymethylacrylamide, N-vinylacetamide, poly (ethylene glycol) methacrylate, or any combination thereof. In one aspect, the crosslinkable monomers and polymers produced therefrom can include N,N-dimethylacrylamide (DMA), N-isopropylacrylamide (NIPAM), and related compounds.

In one aspect, the thermoresponsive polymer includes various polyacrylamides, polyacrylamide derivatives and copolymers thereof. In one aspect, the thermoresponsive polymer is poly-N-isopropylacrylamide, poly-N-n-propylacrylamide, poly-N-n-propylmethacrylamide (32° C.), poly-N-ethoxyethylacrylamide, poly-N-tetrahydrofurfurylacrylamide, poly-N-tetrahydrofurfurylmethacrylamide (~35° C.), poly-N,N-diethylacrylamide (32° C.), poly (C-isopropylacrylamide) and any combination thereof.

In another aspect, the thermoresponsive polymer is poly-N-ethylacrylamide; poly-N-isopropylmethacrylamide; poly-N-cyclopropylacrylamide; poly-N-cyclopropylmethacrylamide; poly-N-acryloyl pyrrolidine; poly-N-acryloyl piperidine; polymethyl vinyl ether; alkyl-substituted cellulose derivatives such as methylcellulose, ethylcellulose, or poly (methyl vinyl ether), poly(pentapeptide).

In one aspect, the thermoresponsive polymer can be poly (N-isopropylacrylamide) (pNIPAAm), poly(N,N-diethylacrylamide) (PDEAAm), poly(N-vinylcaprolactam) (PVCL), poly[2-(dimethylamino)ethyl methacrylate] (PDMAEMA), and any combination thereof.

In one aspect, the thermoresponsive polymer can be non-acrylamide polymers such as poly(2-dimethylamino) ethyl methacrylate (PDMA), poly(vinyl methyl ether) (PVME), poly(N-vinylcaprolactam) (PVCL), poly(2-alkyl-2-oxazoline) (62° C.), poly(2-isopropyl-2-oxazoline) (36° C.), and any combination thereof.

In certain aspects, the thermoresponsive polymer can be blend of two or more different polymers. For example, the composition can include a mixture of a first thermoresponsive polymer and a second thermoresponsive polymer, where each is different.

In certain aspects, the precursor solution can include one or more non-crosslinkable polymers. In one aspect, the non-crosslinkable polymer can be produced in situ. For example, when no crosslinker is present, the crosslinkable monomers when polymerized can produce a non-crosslinkable polymer. In another aspect, when crosslinker is present, the crosslinkable monomers when polymerized can produce crosslinked polymers; however, depending upon the amount of crosslinker that is used, non-crosslinked polymers can also be produced in situ. In another aspect, non-crosslinked polymers can be added to the precursor solution. Examples include, but are not limited to, polyacrylamide, poly(N-isopropylacrylamide), poly(N,N-dimethylacrylamide), polyethylene glycol, hyaluronic acid, and alginic acid.

In one aspect, the gel-phase ink can be from about 1 to about 50 wt % of the crosslinkable monomer, or can be about 1, 5, 10, 15, 20, 25, 30, 35, 40, 45, or about 50 wt % the crosslinkable monomer, or a combination of any of the foregoing values, or a range encompassing any of the foregoing values. In one aspect, the gel-phase ink can be from about 2 to about 30 wt % of the crosslinkable monomer.

In one aspect, the crosslinker has two or more acryloyl groups, methacryloyl groups, or a combination thereof. In one aspect, the crosslinker is a polyalkylene oxide glycol diacrylate or dimethacrylate. For example, the polyalkylene can be a polymer of ethylene glycol, propylene glycol, or block co-polymers thereof. In one aspect, the crosslinker is poly(ethylene glycol diacrylate) (PEGDA). In another aspect, the crosslinker is the crosslinker comprises N,N'-methylenebisacrylamide or N,N'-methylenebismethacrylamide.

In one aspect, the gel-phase ink can be from about 1 to about 50 wt % crosslinker, or can be about 1, 5, 10, 15, 20, 25, 30, 35, 40, 45, or about 50 wt % crosslinker, or a combination of any of the foregoing values, or a range encompassing any of the foregoing values.

In one aspect, when the precursor solution includes PEGDA, the PEGDA can have an average molecular weight of component ethylene glycol diacrylate (EGDA) units from about 170 Da to about 20,000 Da, or can have an average molecular weight of about 170, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10,000, about 10500, about 11,000, about 11,500, about 12,000, about 12,500, about 13,000, about 13,500, about 14,000, about 14,500, about 15,000, about 15,500, about 16,000, about 16,500, about 17,000, about 17,500, about 18,000, about 18,500, about 19,000, about 19,500, about 20,000, or a combination of any of the foregoing values, or a range encompassing any of the foregoing values. In one aspect, the average molecular weight of component EGDA units is from 170 DA to about 20,000 DA, or is from about 170 Da to about 2000 Da, or is from about 170 Da to about 700 Da. In an alternative aspect, PEGDA can be synthesized from polyethylene glycol (PEG) using published procedures in any molecular weight for which PEG can be obtained. In still another aspect, ethylene glycol diacrylate (EGDA), diethylene glycol diacrylate (DEGDA), triethylene glycol diacrylate (TriEGDA), tetraethylene glycol diacrylate (TetEGDA) can be used in addition to or in place of PEGDA.

In another aspect, the gel-phase ink includes PEGDA as a crosslinker and no crosslinkable monomer or crosslinkable polymer. In a further aspect, the gel-phase ink can be from about 1 to about 50 wt % PEGDA, or can be about 1, 5, 10, 15, 20, 25, 30, 35, 40, 45, or about 50 wt % PEDGA, or a combination of any of the foregoing values, or a range encompassing any of the foregoing values. In one aspect, the gel-phase ink can be from about 2 to about 30 wt % PEGDA. In still another aspect, the gel phase ink is from about 5 to about 15 wt % PEGDA. In one aspect, the gel-phase ink is 11 wt % PEGDA (herein referred to as PD).

In one aspect, the precursor solution includes N,N-dimethylacrylamide as a crosslinkable monomer and polyethylene PEGDA as a crosslinker. In a further aspect, the gel-phase ink can be from about 1 to about 50 wt % N,N-dimethylacrylamide, or can be about 1, 5, 10, 15, 20, 25, 30, 35, 40, 45, or about 50 wt % N,N-dimethylacrylamide, or a combination of any of the foregoing values, or a range encompassing any of the foregoing values. In one aspect, the gel-phase ink can be from about 2 to about 30 wt % N,N-dimethyacrylamide. In still another aspect, the gel phase ink is from about 5 to about 15% N,N-dimethylacrylamide. In another aspect, the gel-phase ink can be from about 0.5 to about 2 wt % PEGDA, or can be about 0.5, 1, 1.5, about 2 wt % PEGDA, or a combination of any of the foregoing values, or a range encompassing any of the foregoing values. In one aspect, the gel-phase ink is 10 wt % N,N-dimethylacrylamide and 1 wt % PEDGA (herein referred to as DM).

In still another aspect, the precursor solution includes NIPAM as a crosslinkable monomer and N,N'-methylenebisacrylamide (BIS) as a crosslinker. In a further aspect, the gel-phase ink can be from about 1 to about 50 wt % NIPAM or can be about 1, 5, 10, 15, 20, 25, 30, 35, 40, 45, or about 50 wt % NIPAM, or a combination of any of the foregoing values, or a range encompassing any of the foregoing values. In one aspect, the gel-phase ink can be from about 2 to about 30 wt % NIPAM. In still another aspect, the gel-phase ink is from about 5 to about 15 wt % NIPAM. In another aspect, the gel-phase ink can be from about 0.01 to about 10 wt % N,N'-methylenebisacrylamide, or can be about 0.01. 0.05, 0.1, 0.5, 1, 2, 3, 4, 5, 6, 7, 8, 9, or about 10 wt % N,N'-methylenebisacrylamide, or a combination of any of the foregoing values, or a range encompassing any of the foregoing values. In another aspect, the gel-phase ink can be from about 0.1 to about 5 wt % N,N'-methylenebisacrylamide. In still another aspect, the gel-phase ink can be from about 0.5 to about 2 wt % N,N'-methylenebisacrylamide. In one aspect, the gel-phase ink is 10 wt % NIPAM and 1 wt % N,N'-methylenebisacrylamide (herein referred to as NA+B).

Fugitive Carrier

In one aspect, the fugitive carrier includes a polymer or copolymer. In a further aspect, the copolymer can be a triblock copolymer such as, for example, a polyethylene oxide-polypropylene oxide-polyethylene oxide triblock copolymer (also known as a "poloxamer") where a central hydrophobic polypropylene oxide (PPO) chain is flanked by two hydrophilic polyethylene oxide (PEO) chains.

In one aspect, poloxamer has the formula

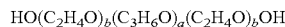

$$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. In one aspect, the poloxamer can be P101, P105, P108, P122, P123, P124, P181, P182, P183, P184, P185, P188, P212, P215, P217, P231, P234, P235, P237, P238, P282, P284, P288, P331, P333, P334, P335, P338, P367, P401, P402, P403, P407 (commercially available from BASF under the trade name PLURONIC® F127), or a combination thereof. Non-limiting examples of poloxamers useful herein include, but are not limited to, those in the table below.

| Copolymer | MW | Average number of EO units | Average number of PO units | CMC (M) |
|---|---|---|---|---|
| F68 | 8,400 | 152.73 | 28.97 | $4.8 \times 10^{-4}$ |
| P103 | 4,950 | 33.75 | 59.74 | $6.1 \times 10^{-6}$ |
| P105 | 6,500 | 73.86 | 56.03 | $6.2 \times 10^{-6}$ |
| P123 | 5,750 | 39.2 | 69.4 | $4.4 \times 10^{-6}$ |
| F127 | 12,600 | 200.45 | 65.17 | $2.8 \times 10^{-6}$ |
| L121 | 4,400 | 10.00 | 68.28 | $1.1 \times 10^{-6}$ |

In one aspect, the polymer or copolymer making up the fugitive carrier is present at from about 15 to about 50 wt % of the gel-phase ink, or is about 15, 20, 25, 30, 35, 40, 45, or about 50 wt % of the gel-phase ink, or a combination of any of the foregoing values, or a range encompassing any of the foregoing values. In another aspect, the polymer or copolymer making up the fugitive carrier is present at from about 22.5 to about 40 wt %, or from about 25 to about 35 wt %. In one aspect, the polymer or copolymer is from about 20 to about 30 wt % of the gel-phase ink. In another aspect, the polymer or copolymer is about 22.5 wt % of the gel-phase ink. In some aspects, the concentration of polymer or copolymer can be above the critical micelle concentration of the polymer or copolymer. In other aspects, the concentration of polymer or copolymer can be equal to the critical micelle concentration. In still other aspects, the concentration of polymer or copolymer can be below the critical micelle concentration.

In some aspects, polymeric material making up the fugitive carrier can be a gel with some solid-like properties at high temperatures, such as, for example, above 10° C., and a liquid or fluid at low temperatures, such as, for example, below about 10° C.

In one aspect, the shear-thinning behavior of the fugitive carrier renders the gel-phase ink 3D printable. In another aspect, the fugitive carrier exhibits a thermally-reversible gel-to-fluid transition. Further in this aspect, the reversible gel-to-fluid transition allows for complete removal of the carrier from printed structures. In another aspect, printed structures of the carrier function as templates to form the primary hydrogels as disclosed herein via polymerization and crosslinking after printing.

In one aspect, the fugitive carrier has shear-thinning properties useful for extrusion-based 3D printing. In one aspect, the fugitive carrier has a shear modulus of from about 10 to about 75 kPa, or has a shear modulus of from about 10 to about 50 kPa, or has a shear modulus of about 10, 15, 20, 25, 30, 35, 40, 45, 50, 55, 60, 65, 70, about 75 kPa, or a combination of any of the foregoing values, or a range encompassing any of the foregoing values. In another aspect, the shear modulus is from about 10 to about 50 kPa. In still another aspect, the shear modulus is from about 15 to about 30 kPa. In one aspect, a higher shear modulus leads to a higher pressure during the 3D printing extrusion process disclosed herein. In one aspect, pressure during extrusion is from about 10 to about 500 kPa, or is about 10, 50, 100, 150, 200, 250, 300, 350, 400, 450, or about 500 kPa, or a combination of any of the foregoing values, or a range encompassing any of the foregoing values. In another aspect, pressure during extrusion is from about 50 to about 400 kPa. In still another aspect, pressure during extrusion is from about 10 to about 300 kPa. In one aspect, changes in concentration of the fugitive carrier can lead to changes in G' and G" of the gel-phase inks (FIG. 1b). In another aspect, structures printed with different concentrations of the fugitive carrier may exhibit different degrees of areal swelling at their top surfaces (FIG. 1i).

Rather than relying on a fugitive carrier, most previous approaches to 3D printability have modified the rheological properties of the printing inks (e.g., through viscosity modulation, pre-crosslinking, addition of nanoparticles, guest-host shear-thinning formulations, etc.) to achieve 3D printability. These modifications couple with and may alter the properties of the final printed hydrogels, or work only for specific hydrogel formulations. In one aspect, the formulations and hydrogels disclosed herein avoid these limitations by making use of a fugitive carrier that allows for 3D printability with a variety of hydrogel precursors.

3D Printability

Figure 9:
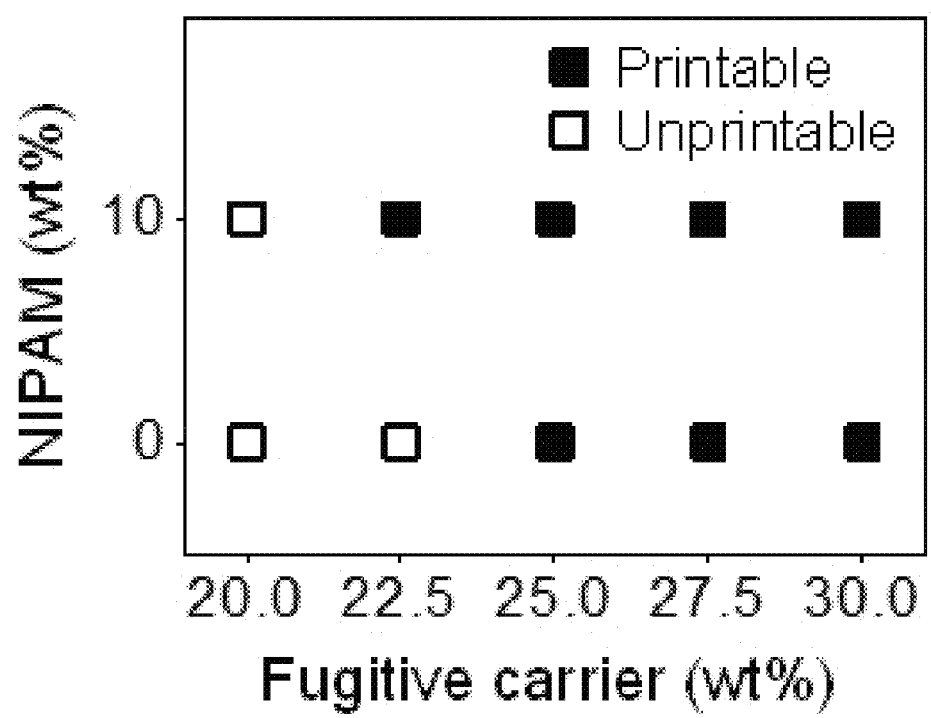
FIG. 9 shows 3D printability of PNIPAM inks (10 wt % NIPAM and 1 wt % PEGDA) with the fugitive carrier (20-30 wt %) and pure fugitive carrier inks (20-30 wt %). The ink (10 wt % NIPAM and 1 wt % PEGDA) with the fugitive carrier (22.5 wt %, slightly above CMC) is 3D printable, whereas the pure poloxamer P367 ink (22.5 wt %) is not 3D printable. The pure poloxamer P407 ink (22.5 wt %) forms droplets at the nozzle during extrusion, resulting in discontinuous, nonuniform filaments.

In one aspect, the fugitive carrier is required for 3D printability, but depending on other components of the gel-phase ink and their concentrations, not all solutions of fugitive carrier are 3D printable. In some aspects, when the concentration of the fugitive carrier is too low (for example, below 22.5 wt %), the gel-phase ink may form droplets during extrusion, resulting in discontinuous filaments. Printability of different gel-phase inks with and without NIPAM and varying concentrations of fugitive carrier are shown in FIG. 9. In some aspects, gel-phase inks may show shear-thinning behavior but poor printability; for example, ink may flow after extrusion and thus generate deformed structures (see FIG. 10a-c).

Figures 10A, 10B, 10C:
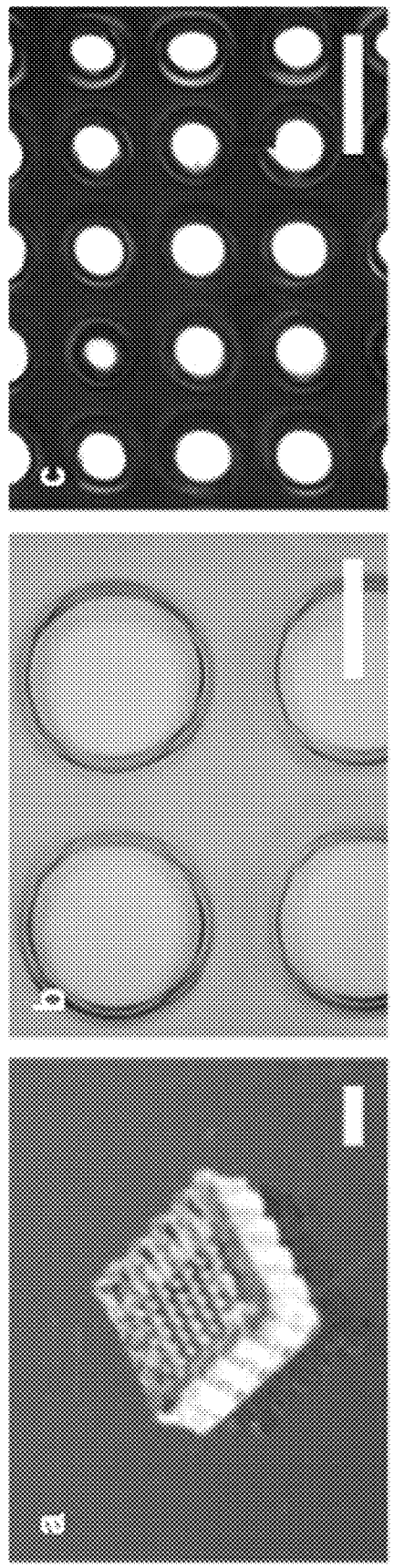
FIGS. 10*a*-10*c* show 3D printing using PNIPAM ink (10 wt % NIPAM and 1 wt % PEGDA) with the fugitive carrier (20 wt %). The concentration of the fugitive carrier in the ink (20 wt %) is lower than its critical micelle concentration (≈21 wt %). 10*a* Optical microscope image of an as-printed 3D lattice structure. The structure shows deformation in the middle (i.e., not self-supporting). Although it shows a shear-thinning behavior, the PNIPAM ink is not 3D printable (based on conditions defined for this study). 10*b* Optical microscope images (top view) of the structure at the swelled state (25° C.). 10*c* Optical microscope image (top view) of the structure at the shrunk state (40° C.). The round shape of the lattice structure indicates that the ink flows after extrusion and forms the meniscus before crosslinking. Scale bars, 2 mm 10*a*; 500 µm 10*b-c*.

In one aspect, the shear-thinning and rapid recovery behavior of the inks disclosed herein with the fugitive carrier (>22.5 wt %) enable high resolution 3D printing of hydrogels (FIG. 1f-h). In a further aspect, these properties allow the inks to be extruded through a 200 μm nozzle while maintaining a filamentary structure after extrusion. In contrast, in some aspects, the ink (10 wt % NIPAM and 1 wt % PEGDA) with the fugitive carrier (20 wt %) below its critical micelle concentration (~21 wt %) shows a shear-thinning behavior (FIG. 1b), but it yields deformed 3D structures with irregular patterns and circular spaces between filaments, reflecting spreading of the ink and the formation of menisci after extrusion (FIG. 10a-c). In any of these aspects, the deformation of as-printed structures indicates that G' of ~14 kPa may not be sufficient to sustain the weight of printed filaments before crosslinking, suggesting a critical modulus (G' of ~15 kPa) required for printing self-supporting 3D structures (FIG. 1b).

Figure 11:
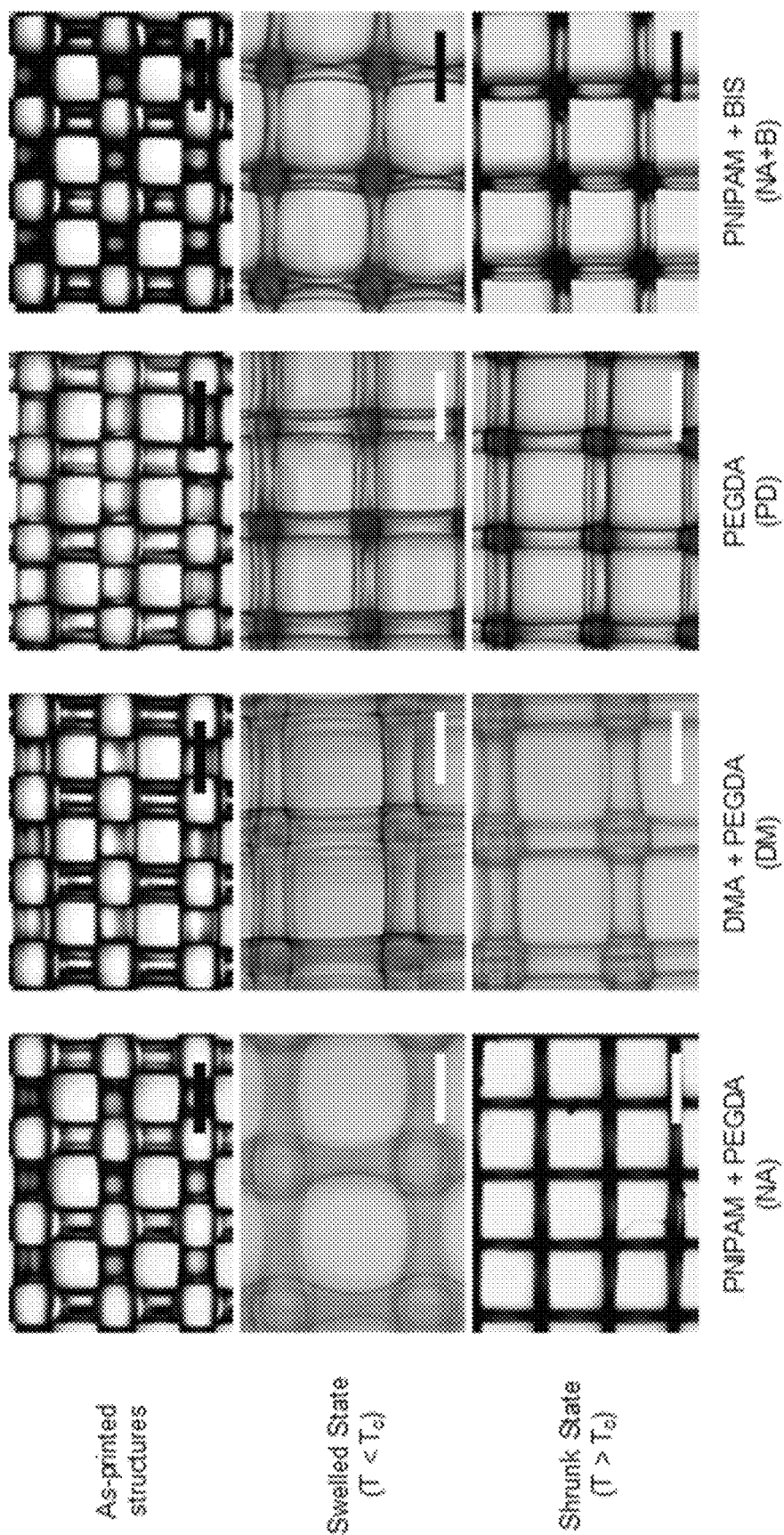
FIG. 11 shows optical microscope images (top view) of multilayer lattice structures printed with the inks shown in FIGS. 1*j*-1*k*. Scale bars 500 µm.

In one aspect, the approaches to 3D printing and printability disclosed herein are generalizable to other photo-crosslinkable hydrogel systems, regardless of physical properties before and after printing. In one aspect, the total weight of gel-phase ink can be from about 1 to about 50 wt %, or can be about 1, 5, 10, 15, 20, 25, 30, 35, 40, 45, or about 50 wt % of the hydrogel system, or a combination of any of the foregoing values, or a range encompassing any of the foregoing values. In another aspect, the total weight of the gel-phase ink can be from about 2 to about 30 wt % of the hydrogel system. In still another aspect, the gel-phase ink can be from about 5 to about 15 wt % of the hydrogel system. In one aspect, 3D hydrogel structures were printed using gel-phase inks containing a fugitive carrier (25.0 wt %) and various precursor solutions: (i) 10 wt % N,N-dimethylacrylamide (DMA) and 1 wt % PEGDA (DM), (ii) 11 wt % PEGDA (PD), and (iii) 10 wt % NIPAM and 1 wt % N,N'-methylene bisacrylamide (BIS) (NA+B). In one aspect, strain-dependent oscillatory rheology of these sample inks shows their shear-thinning properties (FIG. 1j). Further in this aspect, as expected from their rheological properties, all inks are 3D printable, illustrating the versatility of the printing method disclosed herein (FIG. 11). In any of these aspects, the printed structures exhibit the characteristic swelling and shrinking behaviors of the primary hydrogels (FIG. 1k).

Initiator

In another aspect the gel-phase ink includes an initiator. In one aspect, the initiator is a type I photoinitiator such as, for example, 2,2-diethoxyacetophenone, 2-benzyl-2-(dimethylamino)-4'-morpholinobutyrophenone, 4'-tert-butyl-2',6'-dimethylacetophenone, 2,2-dimethoxy-2-phenylacetophenone, a diphenyl(2,4,6-trimethylbenzoyl)phosphine oxide/2-hydroxy-2-methylpropiophenone blend, 4'-ethoxyacetophenone, 3'-hydroxyacetophenone, 4'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, lithium phenyl-2,4,6-trimethylbenzoylphosphinate (LAP), or a combination thereof. In one aspect, the initiator is 2,2-diethoxyacetophenone.

Biological Cells

In one aspect, when the gel-phase ink includes biological cells. In this aspect, the precursor solution and the fugitive carrier are non-toxic to the cells. In some aspects, the cells are present in the gel-phase ink. In other aspects, cells can be added to the materials disclosed herein following the conclusion of the printing process at any stage in the post-printing process including before, after, or during removal of the fugitive carrier. In one aspect, the biological cells are mammalian cells. In another aspect, the biological cells are plant cells.

When the gel-phase ink includes cells, a lower pressure is desired. In one aspect, extrusion pressure is below 150 kPa when the gel-phase ink includes cells, or is below 100 kPa. In a further aspect, extrusion pressure is adjusted based on cell type and nozzle size.

Process for Preparing Gel-Phase Inks

In one aspect, regardless of the monomer, polymer, and/or crosslinker identities, the gel-phase ink contains from about 20 to about 70 wt % solids (i.e., initiator, carrier, monomer, crosslinker), or is about 20, 25, 30, 35, 40, 45, 50, 55, 60, 65, about 70 wt % solids, or a combination of any of the foregoing values, or a range encompassing any of the foregoing values. In another aspect, the gel-phase ink contains from about 25 to about 45 wt % solids. In still another aspect, the gel-phase ink contains from about 25 to about 40 wt % solids. In another aspect, the gel-phase ink further contains a solvent. In one aspect, the solvent is water.

In one aspect, in order to prepare a gel-phase ink according to the present disclosure, the components of the gel-phase ink as disclosed herein are admixed in deionized water with stirring for a period of from about 10 minutes to about 10 hours, or for about 10 minutes, about 30 minutes, or about 1, 2, 3, 4, 5, 6, 7, 8, 9, about 10 hours, or a combination of any of the foregoing values, or a range encompassing any of the foregoing values. In one aspect, use of a mixer enables admixing of components for a shorter period of time such as, for example, about 10 minutes or more. In one aspect, admixing takes place over a period of greater than or equal to 5 hours. In still another aspect, admixing takes place over a period of greater than or equal to 10 hours. In one aspect, the gel-phase ink is prepared at 4° C. with stirring for about 8 hours. Following admixture of the components, in some aspects, the gel-phase inks can be purged with nitrogen or another inert gas to remove air bubbles. In another aspect, following air bubble removal, the gel-phase inks can be stored at a reduced temperature until use. In one aspect, the gel-phase inks are stored at 4° C. overnight.

Methods for 3D Printing of Soft Materials Having Programmed Morphologies and Motions In one aspect, provided herein is a method for extrusion-based 3D printing of soft materials using the gel-phase ink described above. Further in this aspect, prior to printing, the gel-phase inks are loaded into syringe barrels and stored at room temperature. In one aspect, the gel-phase inks are stored at room temperature for a period of from 1 minute to 3 hours prior to printing, or for 1 minute, 10 minutes, 15 minutes 30 minutes, 1 hour, 1.5 hours, 2 hours, 2.5 hours, about 3 hours, a combination of any of the foregoing values, or a range encompassing any of the foregoing values. In another aspect, the gel phase inks are stored at room temperature for about 10 minutes to about 3 hours. In still another aspect, the gel-phase inks are stored at room temperature for about 30 minutes to about 3 hours. In one aspect, the inks are stored in syringe barrels for 2 hours at room temperature prior to printing. Still further in this aspect, the transfer occurs at a temperature at which the inks are in a liquid state, thus facilitating the transfer process.

In one aspect, print paths can be generated by a G-code generator (such as, for example, Slic3r). In an alternative aspect, print paths can be generated manually and can further be simulated and/or reviewed by a simulation software (such as, for example, CAMotics). Following generation of print paths, in one aspect, 3D structures of hydrogels can be printed by an extrusion-based 3D printer featuring at least dual print heads, a UV light-emitting diode (LED) curing system, 200 μm stainless steel nozzles, or a combination thereof. In a further aspect, the 3D structures can be printed at a speed of from 1 to 50 mm/s, or from 1 to 25 mm/s, or from about 1 to about 10 mm/s, or at about 1, 5, 10, 15, 20, 25, 30, 35, 40, 45, or about 50 mm/s, or a combination of any of the foregoing values, or a range encompassing any of the foregoing values. In one aspect, the 3D structures can be printed at a speed of from 1 to 10 mm/s. In another aspect, the 3D structures can be printed at a pressure of from 10 to 500 kPa, or from 50 to 400 kPa, or from 100 to 300 kPa, or can be printed at 10, 50, 100, 150, 200, 250, 300, 350, 400, 450, or about 500 kPa, or a combination of any of the foregoing values, or a range encompassing any of the foregoing values. In one aspect, the printing pressure is from 120 to 280 kPa and is selected based on G' of the printing inks.

In another aspect, the 3D printed structure containing monomer, polymer, crosslinker, fugitive carrier, initiator, and/or cells, is irradiated with UV light following printing to polymerize and/or crosslink the hydrogel precursor molecules (i.e., monomers, polymers, and the like). In one aspect, UV light useful for polymerization and/or crosslinking has a wavelength of 365 nm. In a further aspect, this polymerization and crosslinking results in formation of a hydrogel. Further in this aspect, the hydrogel at this stage still contains the fugitive carrier. In one aspect, the 3D structures are irradiated for from 1 to 10 minutes or longer for the purposes of polymerization and crosslinking. Further in this aspect, the irradiation can be for about 1, 2, 3, 4, 5, 6, 7, 8, 9, about 10 minutes, or a combination of any of the foregoing values, or a range encompassing any of the foregoing values. In one aspect, the 3D printed structures are irradiated for at least 3 minutes.

In one aspect, the fugitive carrier is included in the gel-phase inks disclosed herein to make the compositions disclosed herein 3D printable with existing equipment and can be removed after printing is completed. In one aspect, following printing, polymerization, and crosslinking, the fugitive carrier can be removed from the hydrogel. In a further aspect, the hydrogel structure remains intact upon fugitive carrier removal. In one aspect, the fugitive carrier is soluble in the solvent component of the gel-phase ink. Thus, further in this aspect, if the solvent is water, the fugitive carrier is soluble in water. In one aspect, the fugitive carrier can be removed by immersing the crosslinked structure in water. In a further aspect, the water can be any temperature from 1° C. to 25° C., or can be about 1, 2, 3, 4, 5, 6, 7, 8, 9, 10, 11, 12, 13, 14, 15, 16, 17, 18, 19, 20, 21, 22, 23, 24, about 25° C., a combination of any of the foregoing values, or a range encompassing any of the foregoing values. In one aspect, the water temperature is 4° C. In another aspect, the crosslinked structure can be immersed in water for a period of from about 15 minutes to about 1 hour to remove the fugitive carrier, or can be immersed for 5, 10, 15, 20, 25, 30, 35, 40, 45, 50, 55, about 60 minutes, a combination of any of the foregoing values, or a range encompassing any of the foregoing values. In one aspect, the crosslinked structure is immersed for about 30 minutes to remove the fugitive carrier. In a further aspect, to ensure complete removal of the fugitive carrier, the crosslinked structure can be stored in water for up to 24 h with exchanges of the water every few hours. In another aspect, this storage and water exchange can further ensure the equilibrium shape of the crosslinked structure in the swelled state is reached.

In still another aspect, disclosed herein is a method for creating 3D structures with programmed morphologies and motions using stimuli-responsive anisotropic hydrogels as building blocks. In a further aspect, the stimuli-responsive anisotropic hydrogel building blocks can be linear hydrogel actuators, linear contractile elements, and combinations thereof. In a still further aspect, morphologies and motions for the structures can be programmed based upon the arrangement and construction of their component building blocks.

In one aspect, the method disclosed herein can be used to simultaneously print multiple 3D structures from a single precursor solution in a one-step process. In a further aspect, the method can be used to print multiple 3D structures in a short period of time (such as, for example, in under 1 minute). In still another aspect, the method is highly scalable.

In one aspect, the 3D hydrogel structures disclosed herein include a plurality of filaments. In one aspect, the center-to-center distance between filaments can be from about 100 to about 1000 μm, or can be from about 200 to about 1000 μm, or can be from about 300 to 1000 μm, or can be about 100, 150, 200, 250, 300, 350, 400, 450, 500, 550, 600, 650, 700, 750, 800, 850, 900, 950, about 1000 μm, a combination of any of the foregoing values, or a range encompassing any of the foregoing values. In one aspect, the center-to-center distance between filaments is about 600 μm. In another aspect, the 3D hydrogel structures disclosed herein include one or more layers. In a further aspect, the layer height can be from about 50 to about 400 μm, or can be about 50, 100, 150, 200, 250, 300, 350, or about 400 μm, a combination of any of the foregoing values, or a range encompassing any of the foregoing values. In one aspect, the layer height is about 200 μm. Example 3D printed hydrogel structures are seen in FIG. 11.

In another aspect, disclosed herein is a method for preparing anisotropic hydrogels using 3D printing. In another aspect, temperature-unresponsive polymers such as, for example, polyethylene glycol (PEG) or other crosslinking reinforcement elements are dispersed in a temperature-responsive polymeric matrix according to the processes disclosed herein (FIG. 1a). In one aspect, the PEG crosslinking reinforcement elements are derived from the PEGDA included in the precursor solution of the gel-phase ink. In a similar aspect, other crosslinker identities would result in chemically and/or structurally different reinforcement elements. In one aspect, the anisotropic PEG pattern in the isotropic polymeric matrix restricts stimuli-responsive swelling and shrinkage of the matrix along the direction of continuous PEG filaments (i.e., the "reinforcement direction"), thereby inducing anisotropic actuation perpendicular to the reinforcement direction.

Programmed Motion of 3D Printed Anisotropic Hydrogels

In one aspect, described herein are versatile and simple design rules for creating tunable 3D hydrogel structures. In one aspect, the designs are modular and composed of building blocks such as linear hydrogel actuators. In another aspect, structures are tunable based on the selection of monomer, polymer, and/or crosslinking material as disclosed herein. In an alternative aspect, material properties of the hydrogels may be further based on control of monomer polymerization and crosslinking such as, for example, by varying the length of the crosslinker molecule (e.g., PEGDA), using a mix of crosslinkers, or using a shorter or longer UV exposure time.

In a further aspect, depending on the density and degree of crosslinking of the materials disclosed herein, the degree and/or rate of macroscopic swelling and shrinking of the materials disclosed herein may change, with an increase in density correlating to a reduction in the rates of macroscopic swelling and shrinking. In another aspect, the hydrogels disclosed herein can further move or change shape upon exposure to a chemical agent, UV or visible radiation, a change in solution pH, a change in temperature, a change in ionic strength of the solution in which they are present, a change in pressure, electrical potential, exposure to mechanical stress, exposure to radiation, solvent composition, the presence of biomolecules, or any combination thereof. In one aspect, the as-printed structures disclosed herein (FIG. 1f) may exhibit a swelled state at a low temperature (for example, less than or equal 25° C.; see FIG. 1g) and a shrunken state at higher temperatures such as temperatures >35° C., >40° C., >45° C., or >50° C., or a combination of any of the foregoing values, or a range encompassing any of the foregoing values. In one aspect, as used herein, $T_c$ refers to the volume phase transition temperature of PNIPAM. In a further aspect, $T_c$ is about 32.5° C. In a still further aspect, the swelled state occurs at a temperature <$T_c$ and a shrunken state occurs at a temperature higher than $T_c$. In one aspect, the structures disclosed herein have a shrunken state at temperatures greater than or equal to 35° C. (see FIG. 1h).

In one aspect, disclosed herein are two-dimensional hydrogel sheets with spatially-controlled in-plane growth (e.g., expansion and contraction) that occurs in response to external stimuli. In a further aspect, the in-plane growth can be relied upon to form 3D structures via out-of-plane deformation. In one aspect, the hydrogels disclosed herein can form certain 3D shapes at both the swelled and shrunk states. In one aspect, this property can be harnessed for the purpose of programming growth-induced 3D structures. In another aspect, multiple hydrogel sheets can be stacked or printed on top of one another to form a bilayer or a multilayer structure.

Figure 6:
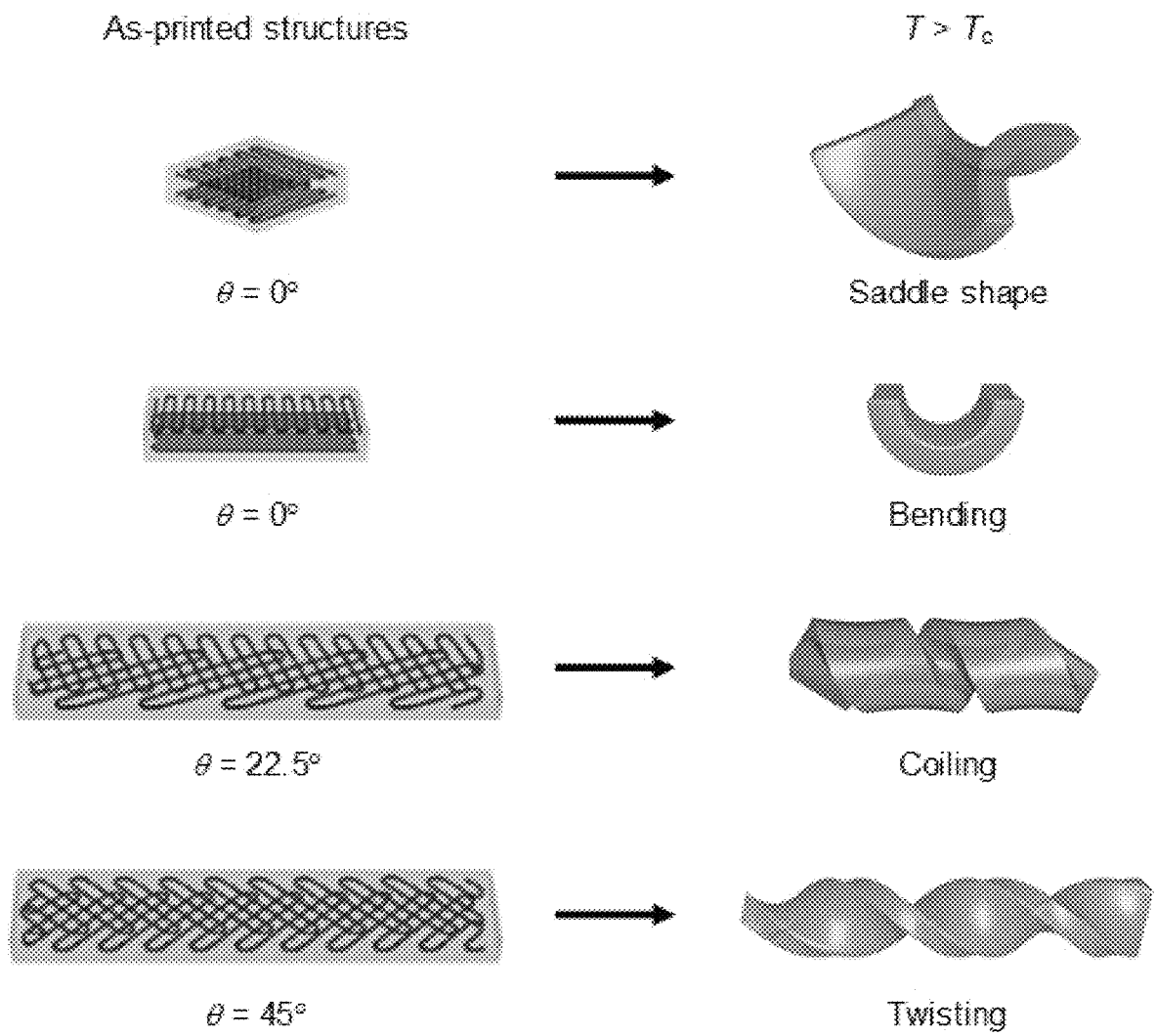
FIG. 6 is a schematic illustration of programming various motions into 3D structures using bilayer structures that consist of orthogonally-oriented linear contractile elements (orthogonally growing bilayer structures). The structures on the left side represent as-printed structures, in which the dark blue lines are PEG reinforcement patterns in PNIPAM hydrogels (light blue). The structures on the right side represent programmed structures at the shrunk state (T>$T_a$). An orthotropically growing bilayer structure with a square shape forms a saddle-like shape at the shrunk state. This saddle-like shape change can be further exploited to produce various motions by controlling the geometry and orientation of the elements. Increasing the aspect ratio of the bilayer structure induces a pure bending-like motion. Controlling the angle θ between the long axis of the structure and the direction of intrinsic curvature produces bending, coiling, and twisting motions with θ of 0°, 22.5°, and 45°, respectively.
Figure 14A:
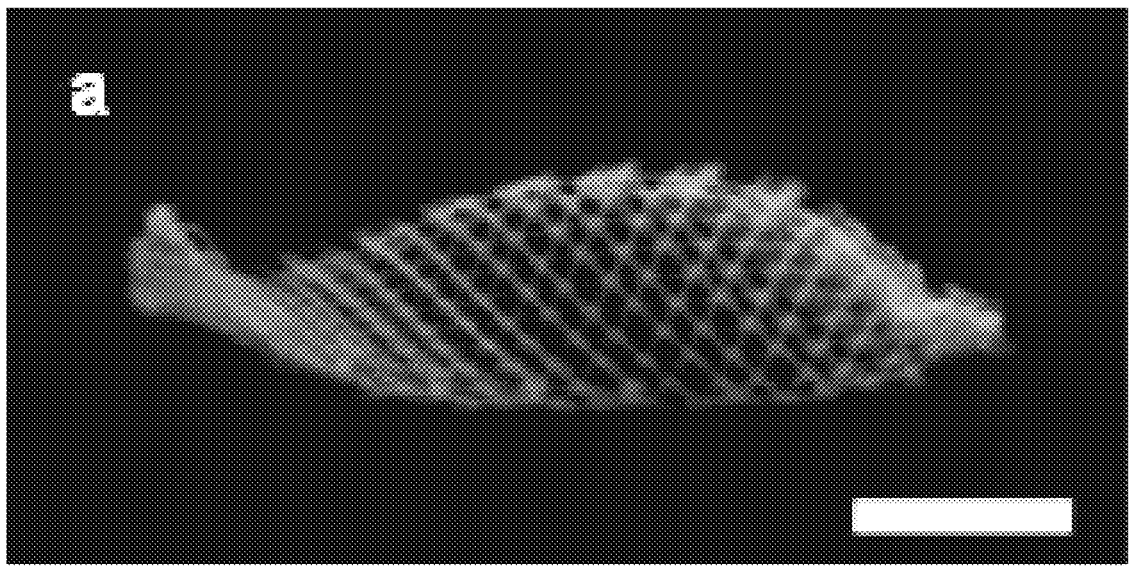
FIGS. 14*a*-14*b* show twisting configurations with θ of 45° 14*a* and 135° 14*b* at the shrunk state, showing reversed handedness. Scale bars 5 mm.
Figure 14B:
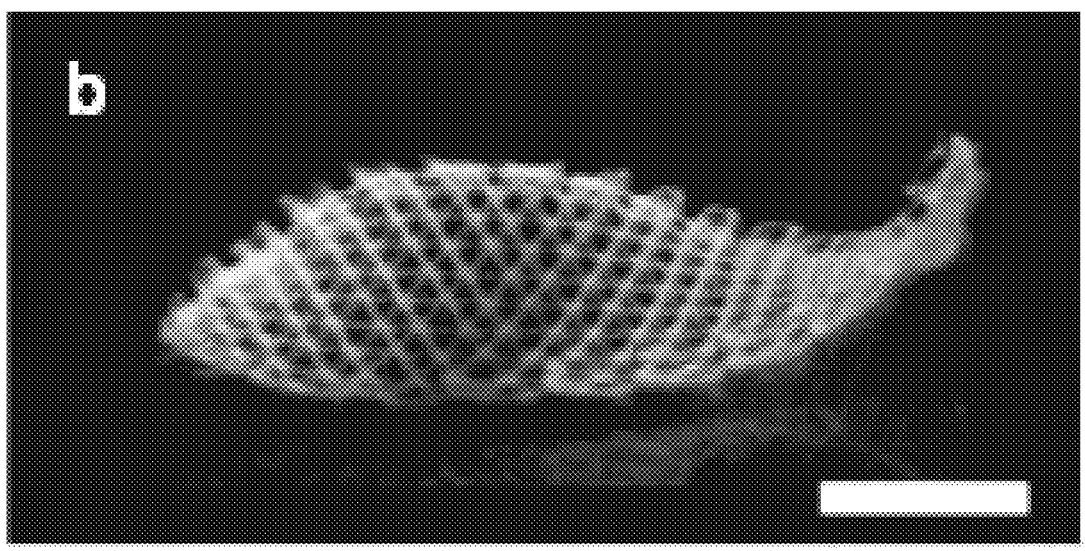

In another aspect, a bilayer structure such as one constructed from the methods disclosed herein, can adopt various shapes and shape changes depending on solution conditions. As an example, orthogonally oriented linear contractile elements can adopt a saddle-like shape (FIG. 1a, FIG. 3a-e, FIG. 13a-d), which can be further exploited to produce various motions from bending to twisting by controlling the geometry and orientation of the elements. In another aspect, increasing the aspect ratio of the bilayer structure induces a pure bending-like motion. In still another aspect, controlling the angle θ between the long axis of formed structures and the direction of intrinsic curvature produces bending, coiling, and twisting motions with θ of 0°, 22.5°, and 45°, respectively. Furthermore, pairing swelling and shrinking actions with an orthogonally growing bilayer structure may, in some aspects, cause a transition from a stretching motion to a bending motion. In one aspect, twisting and hybrid twisting and bending motions with varied pitches can be achieved (FIG. 4a-i, l-n, FIG. 6) and pitch and motion can be predicted based on the width of 3D printed structures (FIG. 4j-k). In a further aspect, handedness of twisted configurations can be controlled by choosing e of different angles. In one aspect, when e has a value of 45°, the printed structures will have an opposite handedness compared to structures where θ is 135° (FIG. 14a-b). In one aspect, as the bilayer structures as disclosed herein transition from a swelled state to a shrunken state (e.g., with an increase in temperature), their motion may further undergo a transition from a stretching-dominated motion to a bending-dominated motion. In many aspects, this transition is reversible upon a decrease in temperature. In some aspects, because individual modules with different parameters can be printed, complex motions can be programmed into the 3D structures disclosed herein through the assembly of multiple functional components, which in turn consist of simple linear contractile elements.

Figure 12:
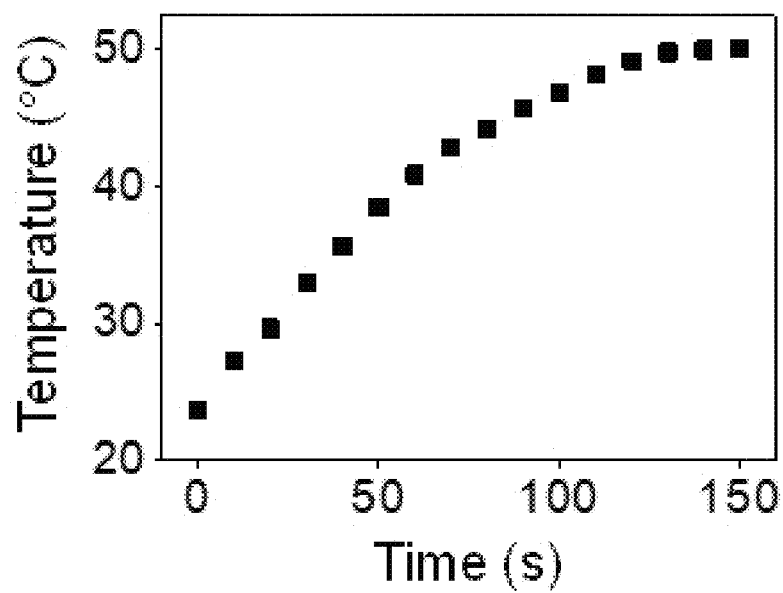
FIG. 12 shows temperature of a solution used to measure the rate of actuation (FIG. 2*e*) as a function of time. The temperature reaches 35.6° C. at 40 s.
Figures 13A, 13B, 13C, 13D:
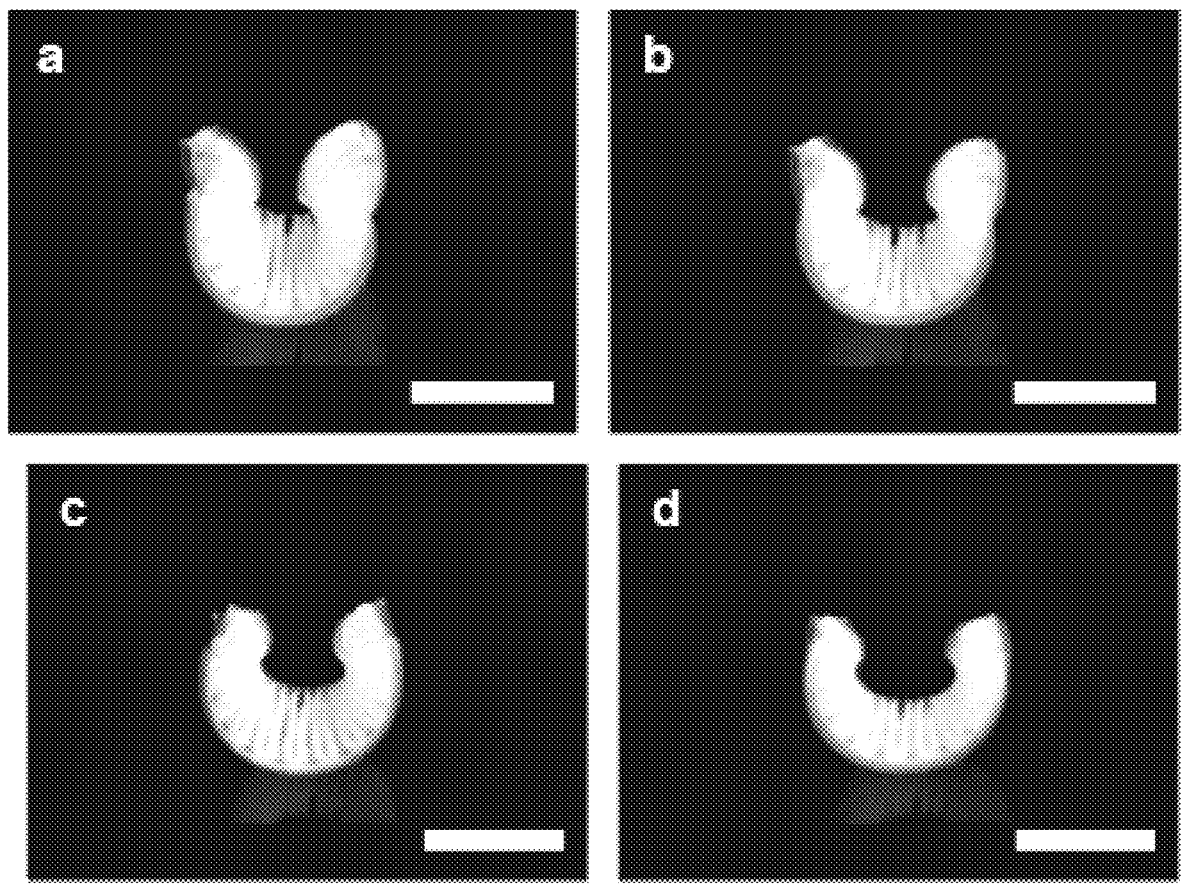
FIGS. 13*a*-13*d* show orthogonally growing bilayer structures with the direction of a principal curvature parallel to the long axis (θ=0°) with different aspect ratios at the shrunk state. The structures have an as-printed length and thickness of 12 mm and 1.6 mm, respectively, and widths of 7.8 mm 13*a*, 6.6 mm 13*b*, 5.4 mm 13*c*, and 4.2 mm 13*d*. Scale bars 5 mm.

In a further aspect, anisotropic actuation can be achieved through temperature cycling and the distances and angles of swelling and structural deformation can be controlled based on as-printed parameters of the hydrogels disclosed herein (FIG. 2a-e, with example embodiments consisting of 2 layers of PNIPAM hydrogels at the base of the hydrogels, 1 layer of PEG on top of those, and 2 layers of PNIPAM hydrogels at the top surface). In one aspect, the rate of actuation can be measured over time with increasing temperature as seen in FIG. 12.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered Aspects, which should not be confused with the claims.

Aspect 1. A gel-phase ink, wherein the gel-phase ink comprises a precursor solution and a fugitive carrier.

Aspect 2. The gel-phase ink of aspect 1, wherein the precursor solution comprises (i) one or more crosslinkable monomers, one or more crosslinkable polymers, or a combination thereof, and (ii) optionally at least one crosslinker or one or more non-crosslinkable polymers, or a combination thereof.

Aspect 3. The gel-phase ink of aspects 1-2, wherein the crosslinkable monomer upon polymerization produces a stimuli-responsive polymer.

Aspect 4: The gel-phase ink of aspects 1-3, wherein the crosslinkable polymer is a stimuli-responsive polymer.

Aspect 5. The gel-phase ink of aspects 3-4, wherein the stimuli-responsive polymer comprises a thermoresponsive polymer, a light-responsive polymer, an ultrasound-responsive polymer, a water-responsive polymer, a biodegradable polymer, a pH-responsive polymer, and any combination thereof.

Aspect 6. The gel-phase ink of aspects 1-5, wherein the crosslinkable monomer comprises 4-pentenoic acid, methacrylamide, vinylphenylboronic acid, acrylamide, N-isopropylmethacrylamide, butyl acrylate, N-vinyl-2-pyrrolidinone, N-hydroxymethylacrylamide, N-vinylacetamide, poly (ethylene glycol) methacrylate, methacrylated hyaluronic acid, or any combination thereof.

Aspect 7. The gel-phase ink of aspects 1-6, wherein the crosslinkable monomers comprise N,N-dimethylacrylamide (DMA), N-isopropylacrylamide (NIPAM), or a combination thereof.

Aspect 8. The gel-phase ink of aspects 1-7, wherein the gel-phase ink can be from about 1 to about 50 wt % of the crosslinkable monomer.

Aspect 9. The gel-phase ink of aspects 1-8, wherein the crosslinker comprises two or more acryloyl groups, methacryloyl groups, or a combination thereof.

Aspect 10. The gel-phase ink of aspects 1-9, wherein the crosslinker is a polyalkylene oxide glycol diacrylate or dimethacrylate.

Aspect 11. The gel-phase ink of aspects 1-10, wherein the at least one crosslinker comprises polyethylene glycol diacrylate (PEGDA), N,N-methylenebisacrylamide (BIS), or a combination thereof.

Aspect 12. The gel-phase ink of aspect 11, wherein the PEGDA has an average molecular weight of from about 200 Da to about 20,000 Da.

Aspect 13. The gel-phase ink of aspect 12, wherein the PEGDA has an average molecular weight of about 575 Da.

Aspect 14. The gel-phase ink of any of aspects 1-13, wherein the precursor solution comprises DMA and PEGDA.

Aspect 15. The gel-phase ink of any of aspects 1-14, wherein the precursor solution comprises PEGDA and does not include any crosslinkable monomers or crosslinkable polymers.

Aspect 16. The gel-phase ink of aspects 1-15, wherein the precursor solution comprises NIPAM and BIS.

Aspect 17. The gel-phase ink of aspects 1-16, wherein the gel-phase ink can be from about 1 to about 50 wt % crosslinker.

Aspect 18. The gel-phase ink of aspects 1-17, wherein the fugitive carrier comprises a copolymer.

Aspect 19. The gel-phase ink of aspect 18, wherein the copolymer comprises a triblock copolymer.

Aspect 20. The gel-phase ink of aspects 1-19, wherein the triblock copolymer comprises a poloxamer.

Aspect 21. The gel-phase ink of aspect 20, wherein the poloxamer has the formula $$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000.

Aspect 22. The gel-phase ink of aspect 20, wherein the poloxamer comprises P101, P105, P108, P122, P123, P124, P181, P182, P183, P184, P185, P188, P212, P215, P217, P231, P234, P235, P237, P238, P282, P284, P288, P331, P333, P334, P335, P338, P367, P401, P402, P403, P407, of a combination thereof.

Aspect 23. The gel-phase ink of aspects 1-22, wherein the poloxamer comprises P407.

Aspect 24. The gel-phase ink of any of aspects 1-23, wherein the fugitive carrier has a shear modulus of from 10 kPa-50 kPa.

Aspect 25. The gel-phase ink of any of aspects 1-24, further comprising a solvent.

Aspect 26. The gel-phase ink of aspect 25, wherein the solvent comprises water.

Aspect 27. The gel-phase ink of any of aspects 1-27, further comprising an initiator.

Aspect 28. The gel-phase ink of aspect 27, wherein the initiator comprises a type I photoinitiator.

Aspect 29. The gel-phase of aspect 27, wherein the initiator comprises 2,2-diethoxyacetophenone, 2-benzyl-2-(dimethylamino)-4'-morpholinobutyrophenone, 4'-tert-butyl-2',6'-dimethylacetophenone, 2,2-dimethoxy-2-phenylacetophenone, a diphenyl(2,4,6-trimethylbenzoyl) phosphine oxide/2-hydroxy-2-methylpropiophenone blend, 4'-ethoxyacetophenone, 3'-hydroxyacetophenone, 4'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, lithium phenyl-2,4,6-trimethylbenzoylphosphinate (LAP), or a combination thereof.

Aspect 30. The gel-phase ink of aspect 27, wherein the initiator comprises 2,2-diethoxyacetophenone.

Aspect 31. The gel-phase ink of aspects 1-30, wherein the gel-phase ink comprises from about 5 wt % to about 15 wt %, or about 10 wt % DMA and from about 0.1 wt % to about 2 wt %, or about 1 wt % PEGDA.

Aspect 32. The gel-phase ink of aspects 1-30, wherein when the gel-phase ink does not include any crosslinkable monomers or polymers, the gel-phase ink comprises from about 5 wt % to about 15 wt %, or about 11 wt % PEGDA.

Aspect 33. The gel-phase ink of aspects 1-30, wherein the gel-phase ink comprises from about 5 wt % to about 15 wt %, or about 10 wt % NIPAM and from about 0.1 wt % to about 2 wt %, or about 1 wt % BIS.

Aspect 34. The gel-phase ink of aspects 1-33, wherein the gel-phase ink comprises from about 20 to about 30 wt % polymer, or about 22.5 wt % polymer.

Aspect 35. The gel-phase ink of any of aspects 1-34, wherein the gel-phase ink possesses shear-thinning properties that allow it to be extruded through a 200 μm nozzle.

Aspect 36. The gel-phase ink of aspect 35, wherein the gel-phase ink maintains a filamentary structure after extrusion.

Aspect 37. The gel-phase ink of aspects 1-36, wherein the gel-phase ink further comprises biological cells.

Aspect 38. A process for preparing the gel-phase ink of any of aspects 1-37, the process comprising:
  a. admixing the precursor solution and fugitive carrier in a solvent to create a first admixture;
  b. stirring at a reduced temperature for a period of time sufficient to thoroughly mix the precursor solution and fugitive carrier; and
  c. purging the first admixture with an inert gas to remove air bubbles.

Aspect 39. The process of aspect 37, wherein stirring is conducted at 4° C. for 8 hours.

Aspect 40. The process of aspect 37, wherein the inert gas is nitrogen.

Aspect 41. A method for extrusion-based 3D printing of soft materials, the method comprising:
  a. loading the gel-phase ink of any of aspects 1-37 into syringe barrels;
  b. storing the syringe barrels at room temperature for about 2 hours;
  c. generating print paths; and
  d. extruding the gel-phase ink from the syringe barrels along the print paths.

Aspect 42. The method of aspect 41, wherein print paths are generated manually or using a G-code generator.

Aspect 43. The method of aspect 41 or 42, wherein printing occurs at a speed of from about 1 to about 4 mm/s.

Aspect 44. The method of aspect 41 or 42, wherein printing occurs at a pressure of from about 120 to about 280 kPa.

Aspect 45. The method of any of aspects 41-44, further comprising irradiating the gel-phase ink with UV light following printing.

Aspect 46. The method of aspect 45, wherein the UV light has a wavelength of 365 nm.

Aspect 47. The method of aspect 45, wherein irradiation is conducted for a period of from about 1 to about 10 min.

Aspect 48. The method of aspect 47, wherein irradiation is conducted for 3 min.

Aspect 49. The method of aspect 45, wherein UV irradiation polymerizes, crosslinks, or polymerizes and crosslinks the gel-phase ink.

Aspect 50. A 3D printed structure produced by the method of any of aspects 41-49.

Aspect 51. A hydrogel produced by the method comprising:
a. 3D printing the gel-phase ink of any of aspects 1-36 on a substrate; and
b. irradiating the gel-phase ink with UV light following printing.

Aspect 52. The method of aspect 51, further comprising removing the fugitive carrier from the hydrogel.

Aspect 53. The method of aspect 52, wherein the method comprises immersing the hydrogel in a solvent for a period of from 15 to 60 minutes at a temperature of from 1 to 25° C.

Aspect 54. The method of aspect 53, wherein the hydrogel is immersed for 30 minutes.

Aspect 55. The method of aspect 53, wherein the solvent is water.

Aspect 56. The method of aspect 55, wherein the water has a temperature of 4° C.

Aspect 57. A hydrogel produced by the method of any of aspects 41-49.

Aspect 58. The hydrogel of aspect 57, wherein the hydrogel comprises a plurality of filaments.

Aspect 59. The hydrogel of aspect 58, wherein the filaments have a center-to-center distance of from about 300 to about 1000 μm.

Aspect 60. The hydrogel of aspect 59, wherein the filaments have a center-to-center distance of 600 μm.

Aspect 61. A multilayer hydrogel comprising two or more layers comprising hydrogels of any of aspects 51-60.

Aspect 62. The multilayer hydrogel of aspect 61, wherein the two or more layers are printed one on top of another.

Aspect 63. The multilayer hydrogel of aspect 61, wherein the two or more layers are assembled after printing.

Aspect 64. The multilayer hydrogel of any of aspects 61-63, wherein the two or more layers have an average layer height of from about 50 to about 400 μm.

Aspect 65. The multilayer hydrogel of aspect 64, wherein the average layer height is about 200 μm.

Aspect 66. The multilayer hydrogel of any of aspects 61-65, wherein the structure can change shape in response to an external stimulus.

Aspect 67. The multilayer hydrogel of aspect 66, wherein the external stimulus comprises exposure to a chemical agent, exposure to light, a change in solution pH, a change in temperature, a change in ionic strength, a change in pressure, electrical potential, exposure to mechanical stress, exposure to radiation, solvent composition, exposure to a biomolecule, or any combination thereof.

Aspect 68. The multilayer hydrogel of aspect 66, wherein the external stimulus comprises a change in temperature.

Aspect 69. The multilayer hydrogel of aspect 68, wherein the multilayer hydrogel exhibits a swelled state at temperatures below 25° C. and a shrunken state at temperatures above 40° C.

Aspect 70. The multilayer hydrogel of any of aspects 66-68, wherein the two or more layers exhibit different responses to the external stimulus.

Aspect 71. The multilayer hydrogel of any of aspects 66-68, wherein the two or more layers exhibit the same response to the external stimulus and are oriented at an angle with respect to one another.

Aspect 72. The multilayer hydrogel of aspects 70-71, wherein the responses of the two or more layers to the external stimulus cause the multilayer hydrogel to undergo a bending, twisting, stretching, or hybrid motion.

Aspect 73. A linear hydrogel actuator comprising the hydrogel of any of aspects 46-49 or the multilayer hydrogel of any of aspects 61-72.

Aspect 74. A modular structure comprising a plurality of the linear hydrogel actuators of aspect 73.

Aspect 75. A method for anisotropic actuation of the modular structure of aspect 74, the method comprising temperature cycling the modular structure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Preparation of Printing Inks

The printing inks consist of a hydrogel precursor solution (11 wt %), a photoinitiator (1 wt % 2,2-diethoxyacetophenone), and the fugitive carrier (25 wt % Pluronic F127). The printing inks for (i) PNIPAM crosslinked with PEGDA, (ii) poly(N,N-dimethylacrylamide) (PDMA), (iii) PEGDA, and (iv) PNIPAM crosslinked with BIS were prepared by dissolving (i) NIPAM (10 wt %) and PEGDA (1 wt %), (ii) N,N-dimethylacrylamide (DMA) (10 wt %) and PEGDA (1 wt %), (iii) PEGDA (11 wt %), and (iv) NIPAM (10 wt %) and BIS (1 wt %), respectively, with 2,2-diethoxyacetophenone (1 wt %) and Pluronic F127 (25 wt %) in deionized water at 4° C. The inks were stirred vigorously for 8 hours at 4° C. The inks were then purged with nitrogen and stored at 4° C. overnight to remove air bubbles before use. Prior to printing, the inks were loaded in 3 mm syringe barrels (Nordson EFD) and stored at room temperature for 2 hours. Because they are in a liquid state, the inks at 4° C. could be easily transferred. All chemicals were purchased from Sigma-Aldrich and used as received.

Rheological Characterization of Inks

Figure 7:
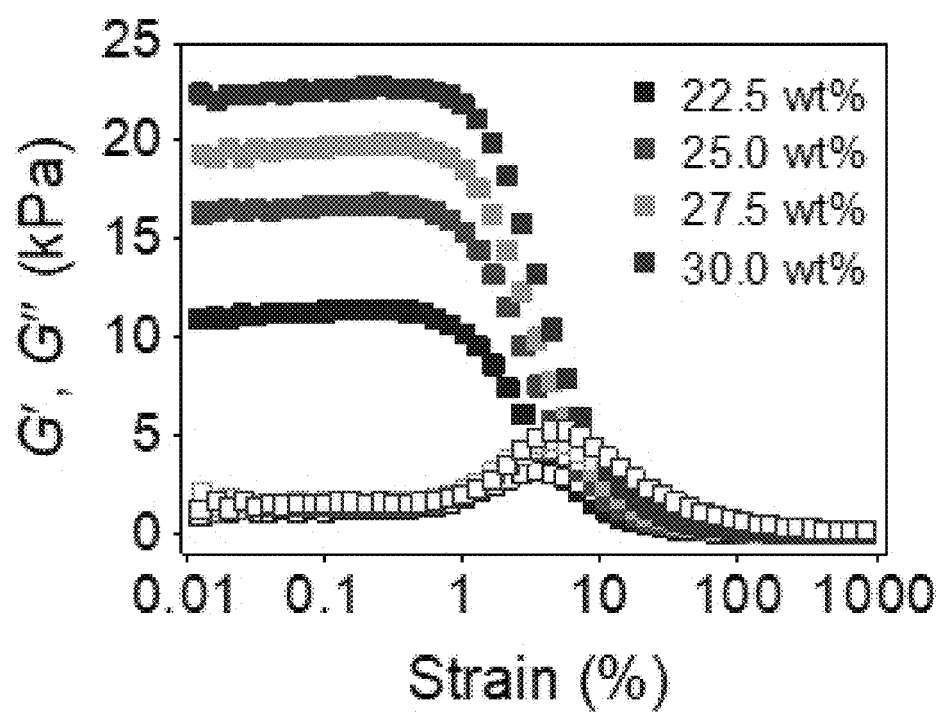
FIG. 7 shows G' and G" of the fugitive carriers (pure poloxamer 407 inks) with different concentrations (22.5-30 wt %) on strain sweeps (0.01%-1000%) at a frequency of 1 Hz, showing shear-thinning properties.
Figures 8A, 8B, 8C, 8D:
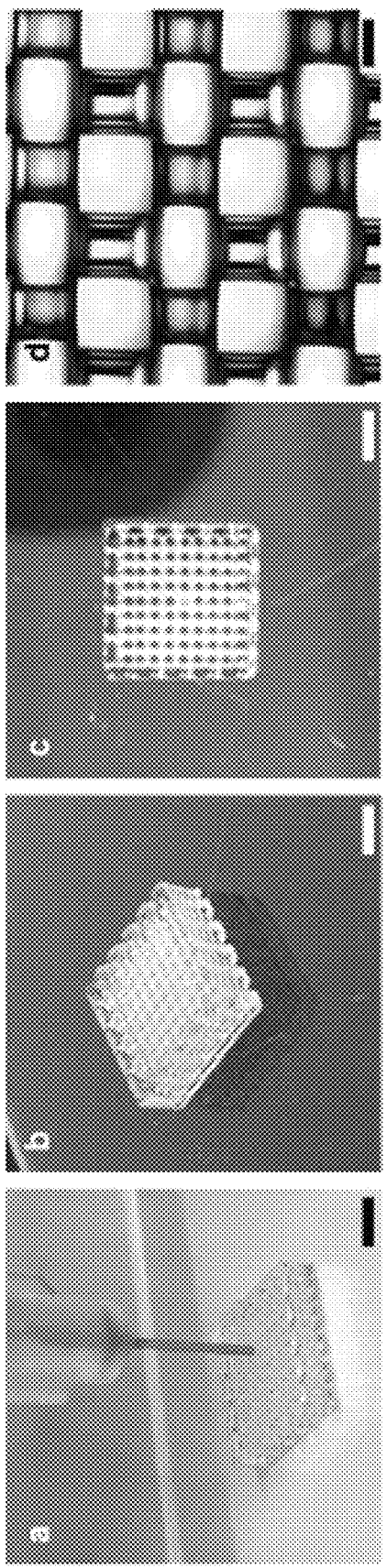
FIGS. 8a-8d show 3D printability of a fugitive carrier ink (25 wt % poloxamer 407). 8a 3D printing process. 8b As-printed lattice structure of the fugitive carrier. 8c Top view of the structure. 8*d* Optical microscope image of the structure. Scale bars, 2 mm 8*a-c*; 200 µm 8*d*.

The rheological properties of the printing inks were measured using a rheometer (DHR-2, TA Instruments) with a 20-mm plate geometry at room temperature. Hydrogel disks of the inks with a diameter of 20 mm were prepared and used at room temperature. To characterize their shear-thinning properties, G' and G" of the inks were measured by oscillatory strain sweeps (0.01-1000%) at a frequency of 1 Hz (FIG. 1j, FIG. 7). To investigate the recovery properties of the inks, step-strain measurements were performed by oscillatory strain steps between 0.5% and 250% at a frequency of 10 Hz (FIG. 1c).

To demonstrate the printing approach disclosed herein, the rheological properties of the inks were investigated (FIG. 1b-c). Gel-phase inks (10 wt % N-isopropylacrylamide (NIPAM) and 1 wt % poly(ethylene glycol) diacrylate (PEGDA)) were designed with the fugitive carrier (20.0-30.0 wt % slightly below and above its critical micelle concentration of ~21 wt %) for printing poly(N-isopropylacrylamide) (PNIPAM) hydrogels. PNIPAM was selected as a model system because of its temperature-responsive volume change useful for building soft actuators. The rheological measurements indicate that the PNIPAM inks are in gel phase (shear storage modulus G'>shear loss modulus G") and have excellent shear-thinning and recovery properties, critical for 3D printing (FIG. 1b, c). The G' value rapidly decreases above critical strain (~1%) and becomes lower than G" (G'-G" crossover) above crossover strain of 4 to 8%, reflecting yielding of the inks and their transition to a liquid-like state (G'<G"), required for extruding the inks (FIG. 1b). The step-strain measurements show the fast recovery of the ink from a liquid-like state (G'<G") to a solid-like state (G'>G") upon reduction of applied strain following shear thinning at high strain (FIG. 1c). The rapid recovery is important for high-resolution 3D printing, as it prevents the flow of the ink after extrusion (often observed in liquid-phase inks). In addition, the G' value of the inks is high enough to support as-printed structures before crosslinking (G'>~15 kPa at low strain).

3D Printing of Hydrogels

A. 3D Printing Process

The 3D printing process is illustrated in FIG. 1d, FIG. 5, and FIG. 8a-d. Print paths were generated by a G-code generator (Slic3r) or manually and simulated and reviewed by a simulation software (CAMotics). 3D structures of hydrogels were printed by an extrusion-based 3D printer with dual print heads and ultraviolet (UV) light-emitting diode (LED) curing systems (Inkredible+, Cellink) using 200-μm stainless steel nozzles (Nordson EFD) at room temperature. The 3D structures were designed to have a center-to-center distance between filaments of 600 μm and a layer height of 200 μm. The 3D structures were printed at a printing speed of 1 to 4 mm s$^{-1}$ and printing pressure of 120 to 280 kPa, depending on G' of printing inks. After printing, the 3D structures were irradiated by UV light (365 nm) for 3 minutes or longer to polymerize and crosslink the precursor solutions.

B. Printed Structures

Figure 5:
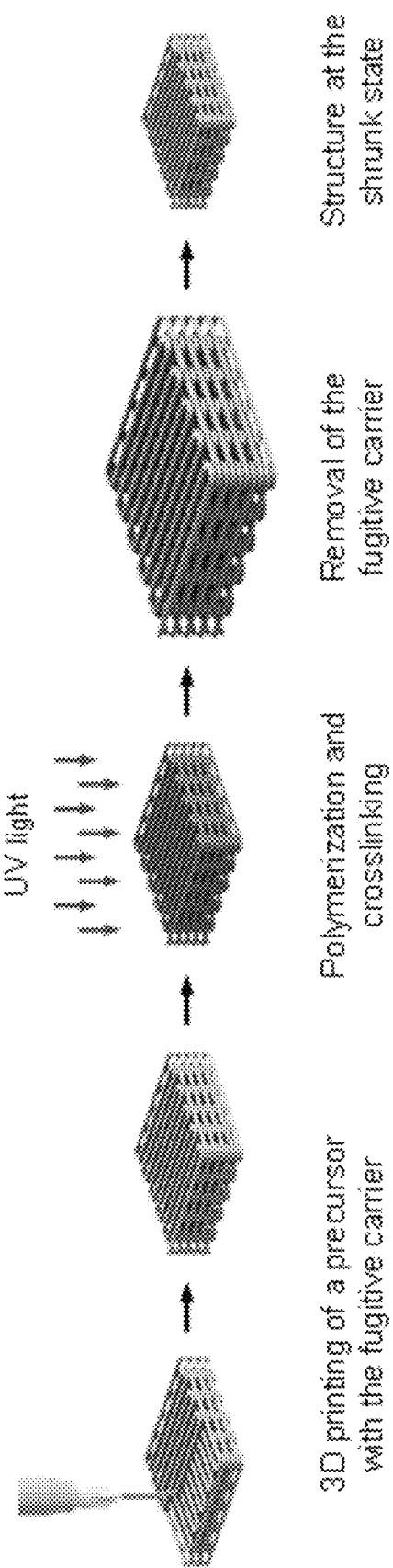
FIG. 5 is a schematic illustrating 3D printing of hydrogels from low viscosity precursor solutions using a gel-phase fugitive carrier with shear-thinning properties. A 3D structure of a hydrogel is printed with a gel-phase ink (hydrogel precursor with the fugitive carrier). The printed 3D structure is then irradiated by UV light to polymerize and crosslink the hydrogel precursor within the printed structure. After forming the primary hydrogel, the fugitive carrier is removed by immersing the crosslinked structure in water at 4° C. The resulting 3D structure, composed of a PNIPAM hydrogel, reversibly changes the volume in response to temperature change.

To demonstrate 3D printability of the inks disclosed herein, multilayer lattice structures were printed using a 200 μm nozzle (FIG. 1d, FIG. 5). The inks that produce well-defined, self-supporting multilayer structures are defined as 3D printable. The PNIPAM inks with the fugitive carrier (>22.5 wt %) show excellent 3D printability (FIG. 1d, FIG. 7). After printing, PNIPAM networks were formed within the printed structures through photopolymerization and crosslinking as described above, using the printed filaments of the carrier as a template. The carrier was then removed by immersing the structures in water at 4° C. for 30 minutes. To completely remove the fugitive carrier and achieve the equilibrium shapes at the swelled state, the structures were further stored in water at 4° C. for 24 hours while exchanging the water every several hours.

Figures 2A, 2B:
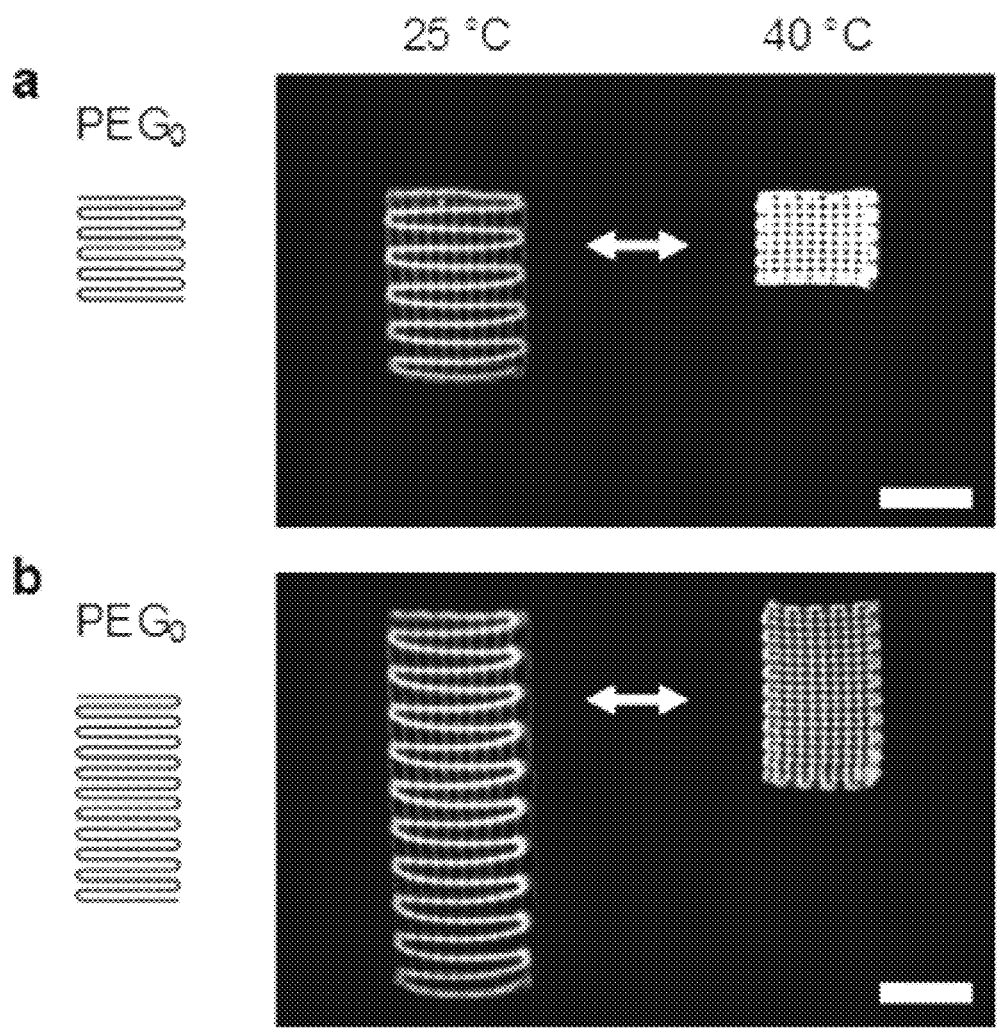
FIGS. 2a-2e show 3D structures of hydrogels with anisotropic actuation. 2a Hydrogel linear actuator with an as-printed length and width of 6 mm. 2b-d Hydrogel linear actuators with an as-printed length and width of 12 mm and 6 mm, respectively, that actuate in the direction at 0° 2b, 90° 2c and 45° 2d with respect to the long axis. The structures 2a-d consist of 2 layers of PNIPAM hydrogels, 1 layer of PEG pattern, and 2 layers of PNIPAM hydrogels from the bottom layer to the top layer and have an as-printed thickness of 1 mm. The figures show the schematics of PEG patterns (dark blue lines) in PNIPAM hydrogels of as-printed structures (left), the PNIPAM structures with PEG patterns (shown in dark blue lines) at the swelled state (middle), and the structures at the shrunk state (right). 2e Changes in the relative length $\Delta L/\Delta L_0$ of the structure shown in 2e (black squares; as-printed thickness of 2 mm) and the linear actuators shown in 2b (red squares) and 2c (blue squares) upon rapid increase in temperature from 24 to 50° C. $\Delta L/\Delta L_0=(L-L_{50})/(L_{24}-L_{50})$, where L, $L_{50}$, and $L_{24}$ are the lengths of the structures at the time of measurement, at the shrunk state (T=50° C.), and at the swelled state (T=24° C.), respectively. The dashed line indicates the time when the solution temperature reaches ~35° C. The closed and open squares represent the relative lengths along the major actuation and transverse directions, respectively. Scale bars 5 mm.
Figures 2C, 2D:
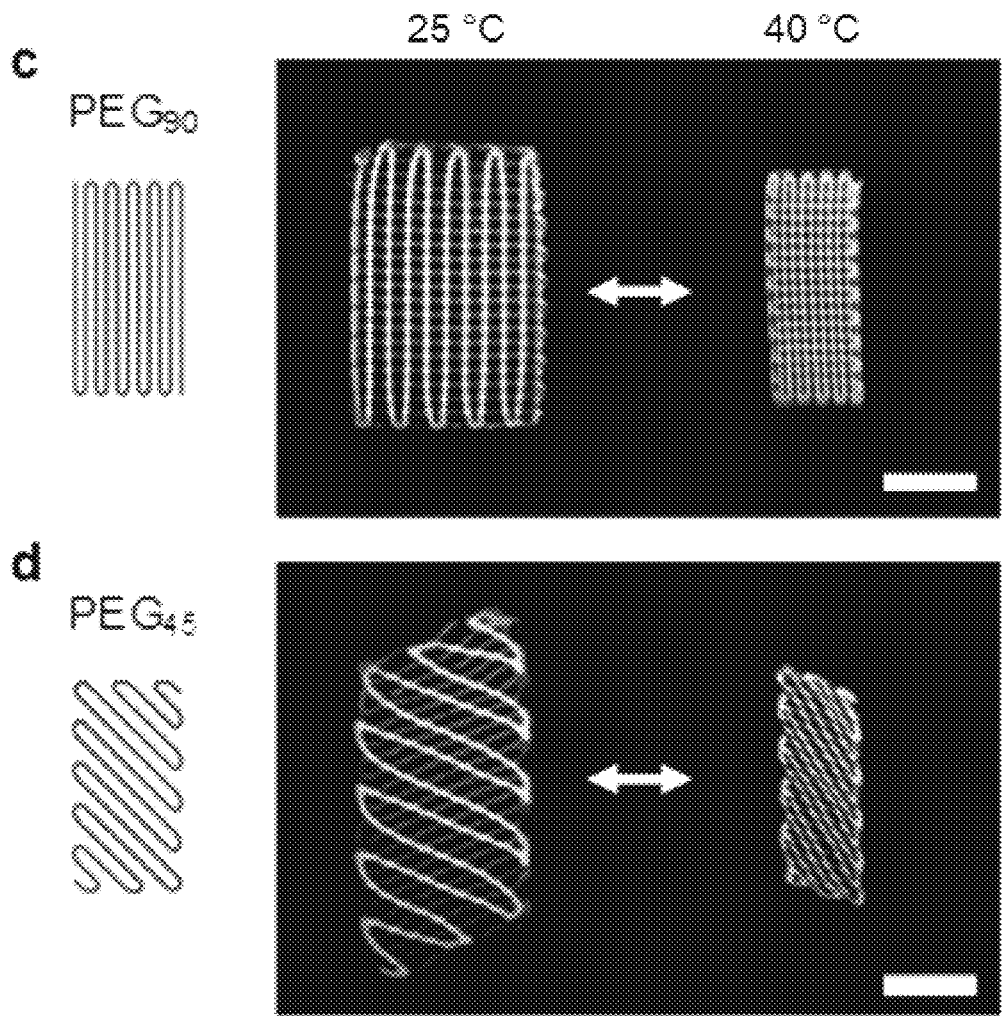
Figure 2E:
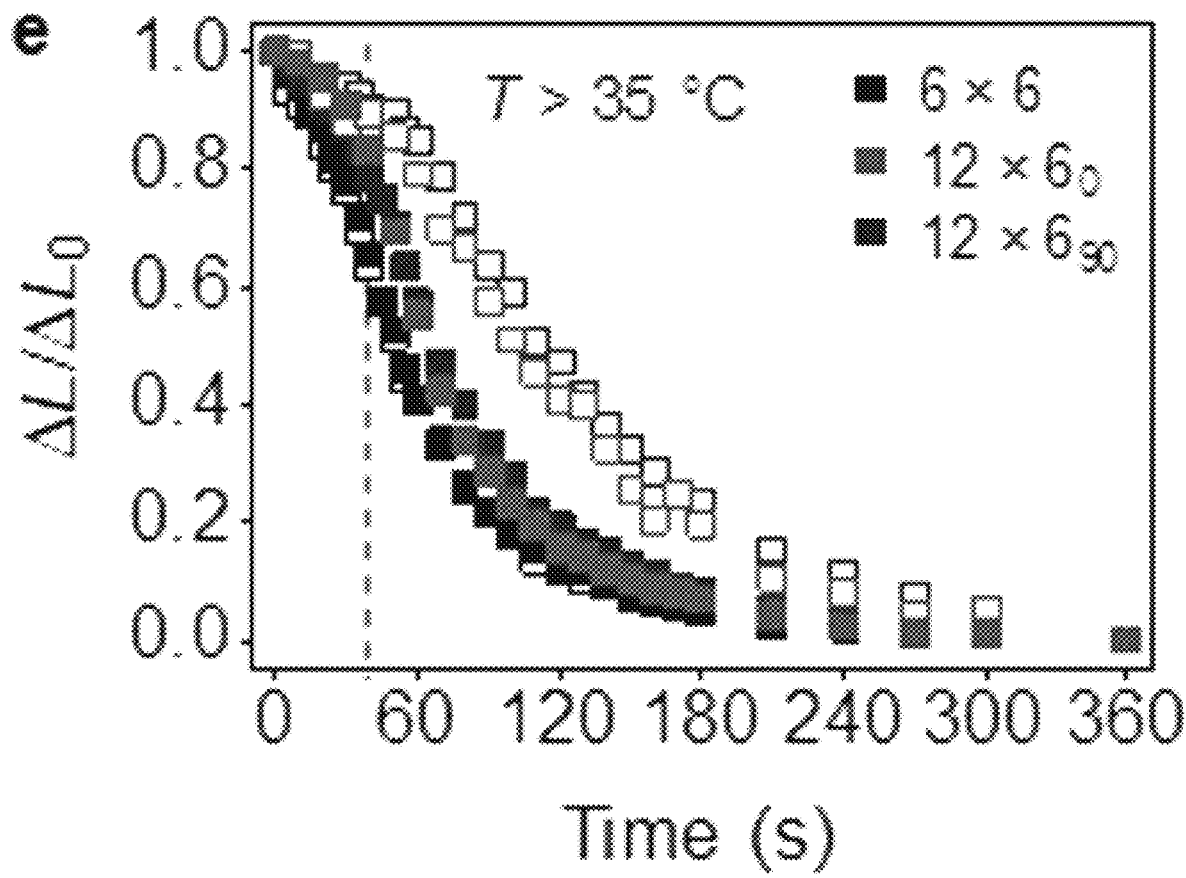

Taking advantage of the 3D printing method as described herein, 3D structures with anisotropic actuation (linear contractile elements) were created using two types of hydrogels (FIG. 2a-d). Inspired by biological anisotropic tissues, anisotropic PEG patterns were printed in isotropic PNIPAM matrices, in which the PEG patterns work as artificial reinforcing elements (FIG. 2a-d). The PEG patterns were printed in the middle layer of the structures to prevent bending and achieve pure stretching motions. The basic concept is to restrict the swelling and shrinking of PNIPAM structures in the reinforcement direction, as observed in anisotropic biological tissues (e.g., those of pine cones, wheat awns, and Bauhinia seed pods reinforced with cellulose microfibrils). As designed, the 3D structures with anisotropic PEG patterns linearly actuate by ~210% in the direction perpendicular to the PEG reinforcement (FIG. 2a-d). The actuation in the longitudinal direction (~110% strain), the major actuation direction, from a shrunk state to a swelled state is around 6-fold higher than the actuation in the transverse direction (~20% strain). The direction of actuation can be controlled by the orientation of PEG patterns (FIG. 2a-d). In addition to anisotropic actuation, the 3D structures show a high rate of actuation (~75% min$^{-1}$ in the linear range) compared to conventional 3D hydrogel structures (FIG. 2e, FIG. 12). This rate is much higher than that of homogeneous PNIPAM hydrogels (e.g., ~60 min required for 15% volume shrinkage for 2 mm-thick disks) and comparable to those of fast responsive hydrogels, such as nano-structured hydrogels (>2 min required for 50% volume shrinkage for 10 mm-thick disks) and nanocomposite cryogels (typically >5 min for 50% volume shrinkage for cylindrical hydrogels with diameter of 6 mm). The interfilament microchannels facilitate the transport of water through 3D structures, leading to fast actuation.

C. Temperature-Responsive Shape Changes

The temperature-responsive shape changes of 3D printed structures were characterized in a temperature-controlled water bath. The resulting 3D structures, thus composed of pure PNIPAM hydrogels, exhibit the characteristic volume change behavior while maintaining their lattice structures (FIG. 1e-h). The concentration of the carrier does not affect the behavior (FIG. 1i). The precursor solutions without the carrier are low viscosity liquids and thus not 3D printable.

Figures 3A, 3B, 3C, 3D, 3E:
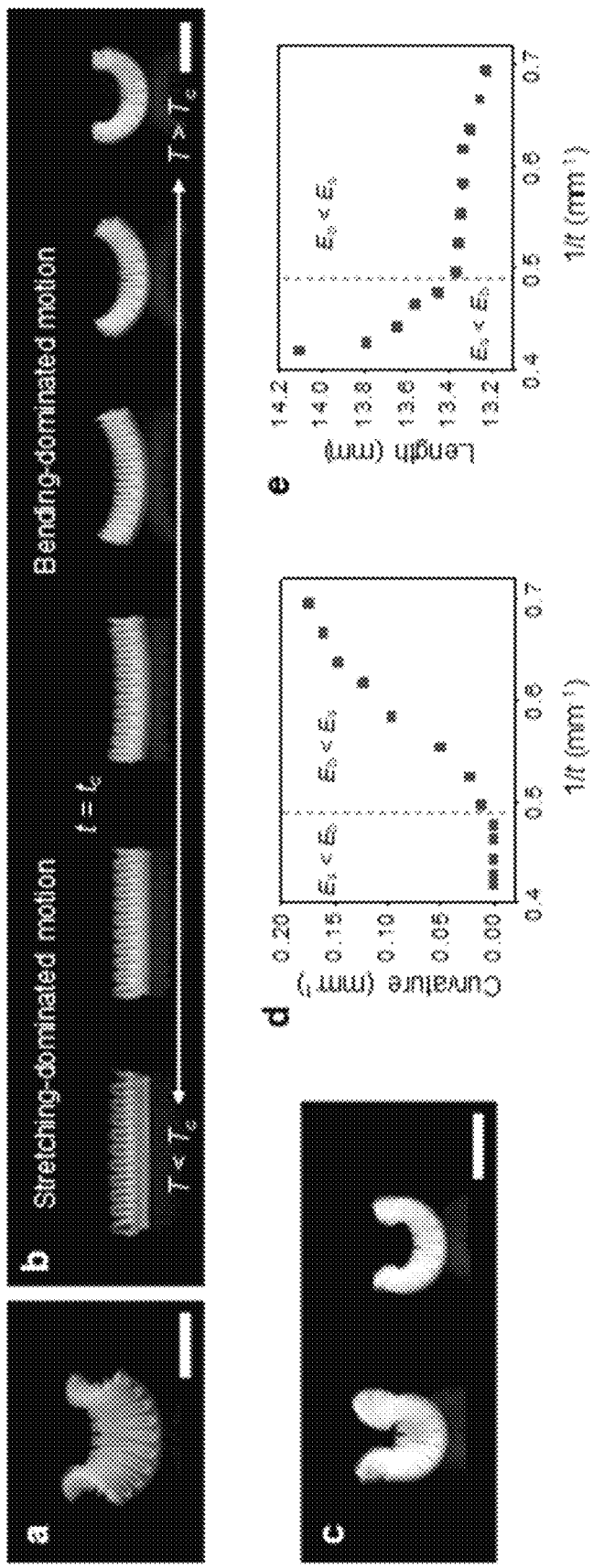
FIGS. 3a-3e show orthogonally growing bilayer structures with a saddle-like shape change and bending motion. 3a Saddle-like shape of an orthogonally growing bilayer structure (as-printed size: 12×12 mm) at the shrunk state. 3b Bending motion of an orthogonally growing bilayer structure with a high-aspect ratio (as-printed size: 12×4.2 mm) along the long axis upon temperature increase from 25 to 40° C. 3c Bending of orthogonally growing bilayer structures with a low aspect ratio (left; as-printed size: 12×7.8 mm) and a high aspect ratio (right; as-printed size: 12×4.2 mm) at the shrunk state. The structures in 3a, 3b, and 3c have an as-printed thickness of ~1.6 mm. 3d-e Curvature 3d and length 3e of the structure shown in 3b along the long axis as a function of 1/t. Scale bars 5 mm.

It was next explored whether 3D structures can be designed with programmed motions through the modular assembly of linear contractile elements (FIG. 3a-e). This strategy takes the inspiration from plant organs that achieve various movements using a bilayer structure of orthogonally oriented tissues with uniaxial swelling and shrinking behaviors. Thus, such an orthotropically growing bilayer structure with a square shape was considered (FIG. 3a). The structure was constructed by printing a linear contractile element (e.g., one shown in FIG. 2a) on top of another element in the perpendicular direction. The structure reversibly transforms its configuration from a near-planar shape at the swelled state to a saddle-like shape with two principal curvatures with opposite signs (Gaussian curvature K=k$_1$k$_2$<0, where k$_1$ and k$_2$ are principal curvatures) at the shrunk state (FIG. 3a).

D. Theoretical Model

To understand the shape change, such an orthogonally growing bilayer structure was theoretically considered. The theoretical model based on the elastic energy equivalence between an orthogonally growing bilayer structure and a curved monolayer structure, energetically equivalent to the bilayer structure, provides the relationship between them:

$$a_r = \frac{1}{2}(a_1 + a_2), \quad b_r = \frac{3}{4t}(a_1 - a_2), \tag{1}$$

where a$_r$ and b$_r$ are the first and second fundamental form (reference metrics) of the equivalent monolayer structure in a strain-free configuration, a$_1$ and a$_2$ are the first fundamental forms of the individual layers (linear contractile elements) of the bilayer structure, and t is the thickness of the structures. The energetically equivalent monolayer structure represents the midsurface of the bilayer structure. In general, the actual configuration of the bilayer structure is not strain free and thus the metrics of its midsurface $a_c$ and $b_c$ are close to but can be different from $a_r$ and $b_r$ ($a \neq a$, or $b \neq b_r$). The structure adopts a residually strained configuration of minimum energy determined by a competition between stretching and bending energies. The orthogonally oriented linear contractile elements have the metrics in the form $$a_1 = \begin{pmatrix} \beta^2 & 0 \\ 0 & \alpha^2 \end{pmatrix}, a_2 = \begin{pmatrix} \alpha^2 & 0 \\ 0 & \beta^2 \end{pmatrix}, \quad (2)$$

where $\alpha$ and $\beta$ are the linear growth (swelling or shrinking) factors in the longitudinal (major actuation) and transverse directions, respectively. The metrics of the strain-free monolayer structure, energetically equivalent to the orthogonally growing bilayer structure, can thus be obtained from Equation 1 and 2

$$a_r = \frac{\alpha^2 + \beta^2}{2} \begin{pmatrix} 1 & 0 \\ 0 & 1 \end{pmatrix}, b_r = \frac{3(\alpha^2 - \beta^2)}{4t} \begin{pmatrix} -1 & 0 \\ 0 & 1 \end{pmatrix}. \quad (3)$$

These metrics adopt the Gaussian and mean curvatures $$K = -\frac{9}{4t^2} \left( \frac{\alpha^2 - \beta^2}{\alpha^2 + \beta^2} \right)^2 = -k_0^2, H = 0, \quad (4)$$

where $K = \det(a_r^{-1} b_r)$, $H = (\frac{1}{2}) \operatorname{trace}(a_r^{-1} b_r)$, and $k_0$ is a principal curvature. The model suggests that an orthogonally growing bilayer structure induces a saddle-like shape ($K = k_1 k_2 < 0$ and $k_1 = k_0 \sim -k_2$) for any anisotropic growth factors ($\alpha \neq \beta$), as observed in the experimentally created structure (FIG. 3a). For typical values of $\alpha = 0.85$ and $\beta = 1.05$ of the linear contractile elements (FIG. 2) and $t = 1.5$ mm of a bilayer structure, the model provides $k_0 = 0.20$ mm$^{-1}$, which agrees well with an experimentally measured $k_1$ of $\sim 0.18$ mm$^{-1}$ (FIG. 3a). The model also predicts $k_1 = -k_2$ and thus $H = 0$. However, the experimental structure has $k_1 > -k_2 = \sim 0.12$ mm$^{-1}$. This behavior is attributed to the interaction between the structure and the substrate, which decreases $k_2$ along the second principal axis.

E. Types of Motion

Inspired by natural hygromorphs, the saddle-like shape change was next converted into bending motion (FIG. 3b). For example, the pine cone scale consists of two tissue layers reinforced perpendicular and parallel to its long axis in a bilayer configuration with a high aspect ratio. As the layer reinforced parallel to the long axis restricts its swelling along the long axis and the other layer does not, the reinforcement architecture induces humidity-driven bending in the opening and closure of the pine cone. As observed in the pine cone scale, increasing the aspect ratio of the orthogonally growing bilayer structure along the direction of a principal curvature ($\theta = 0°$) induces bending motion along the long axis FIG. 3b). As the aspect ratio increases, the equilibrium configurations of the bilayer structures at the shrunk state transform from a saddle-like shape (FIG. 3a) to an arc shape (FIG. 3b-c; FIG. 13). The structure with a high aspect ratio generates bending motion, macroscopically similar to pure bending along the long axis, while preserving the second curvature (bending) along the short axis.

An important finding is that the bilayer structure undergoes a transition between a stretching dominated motion and a bending dominated motion during its shape transformation (FIG. 3b). Although the linear contractile elements disclosed herein yield significant anisotropic swelling (FIG. 2), the bilayer structure forms a near-planar shape at the swelled state ($T < T_c$), presumably because of the relatively large t (FIG. 3b). As the stretching and bending energies scale $E_s \sim t$ and $E_b \sim t^3$, respectively, it is expected that stretching-dominated motion is energetically favorable at the swelled state ($E_s < E_b$), if t is larger than a critical thickness $t_c$. Thus, as it shrinks, the bilayer structure indeed undergoes a transition from a stretching-dominated (linear contractile) motion ($t > t_c$) to a bending-dominated (pure bending-like) motion ($t < t_c$) at $t_c = \sim 2.1$ mm (FIG. 3b). To further elucidate this mechanism, the curvature and length of the structure were monitored as a function of t during its shape transformation (FIG. 3d-e). The curvature k shows a clear transition from a linear contractile motion (k=0) to a bending motion (k~1/t) at $t_c = \sim 2.1$ mm (FIG. 3d). More interestingly, the rate of length change makes a transition from $dl/d(1/t) < 0$ to $dl/d(1/t) \sim 0$ at $t_c = \sim 2.1$ mm. These behaviors indicate that the bending motion is less costly than the linear contractile motion at $t < t_c$. The structure thus tends to preserve its length at $t < t_c$ (FIG. 3e). The residual stress developed by the metric incompatibility is therefore mostly relieved by out-of-plane bending at $t < t_c$. This mechanism differs from that of bimorph bending (e.g., bimetallic thermostats) with a single curvature induced by the differential growth of the two layers in the same direction ($K \geq 0$, $H \neq 0$). In contrast, the bending motion in this study is driven by the competition between stretching and bending energies ($K < 0$, $H \sim 0$).

Figures 4A, 4B, 4C, 4D, 4E, 4F, 4G, 4H, 4I:
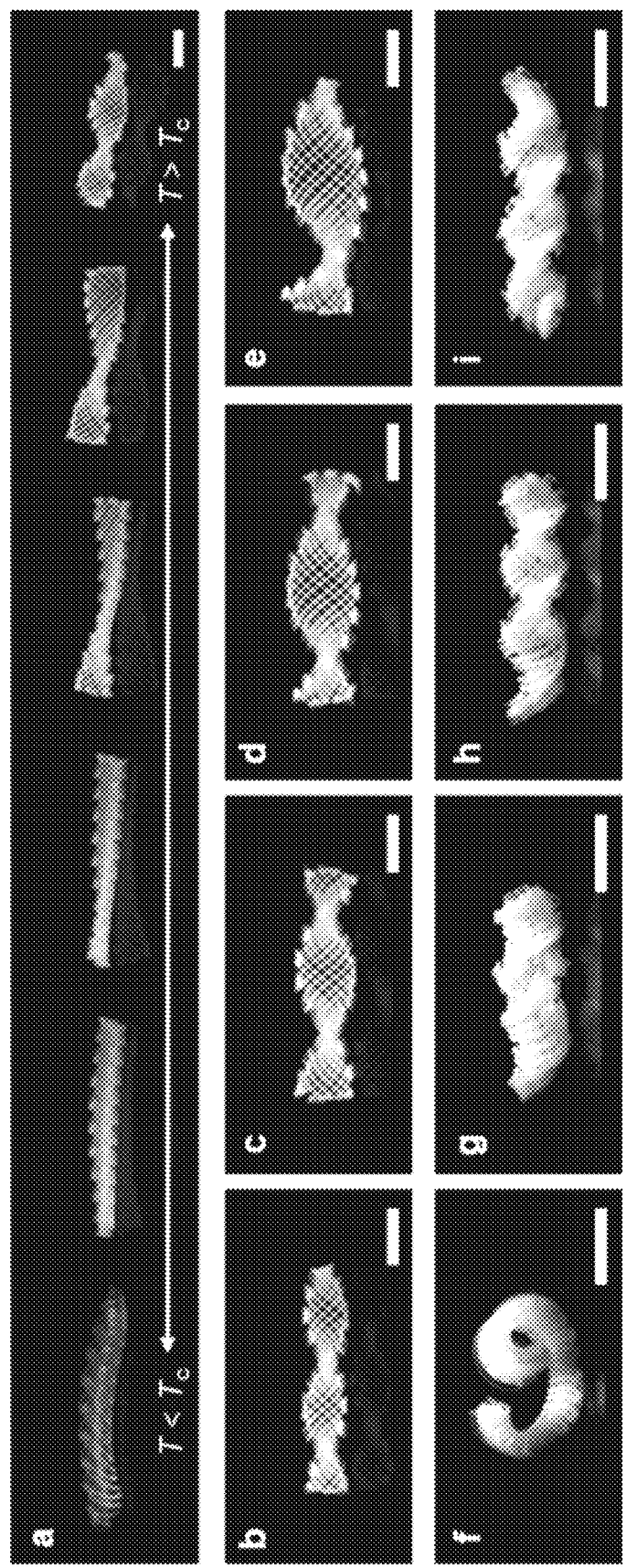
FIGS. 4a-4n show programming of complex motions based on the materials and methods disclosed herein. 4a Twisting motion of an orthogonally growing structure. 4b-e Twisting motions of orthogonally growing structures with an as-printed length and thickness of 24 mm and 1.6 mm, respectively, and width of 4.2 mm 4b, 5.4 mm 4c, 6.6 mm 4d, and 7.8 mm 4e. The figures show the structures at the shrunk state (T>$T_c$). 4f-i Hybrid bending and twisting motions of orthogonally growing bilayer structures (as-printed size: 24 mm, 4.2 mm, and 1.4 mm in length, width, and thickness, respectively) with θ of 0° 4f, 22.5° 4g, 33.75° 4h and 45° 4i. 4j Pitch of the structures shown in 4b-e as a function of width. The dashed line shows a linear fitting (p=4w). 4k Pitch of the structures shown in 4f-i as a function of θ. The dashed line shows the theoretical prediction based on the seed pod model p=(2π/$k_0$) sin 2θ. 4l-m Twisting configurations with θ of 22.5° 4l and 112.5° 4m, showing reversed handedness. 4n Multimodular 3D structure with multiple functional components, showing hybrid motions in response to temperature change from T<$T_c$ (left) to T>$T_c$ (right). Scale bars 5 mm.
Figures 4J, 4K, 4L, 4M, 4N:
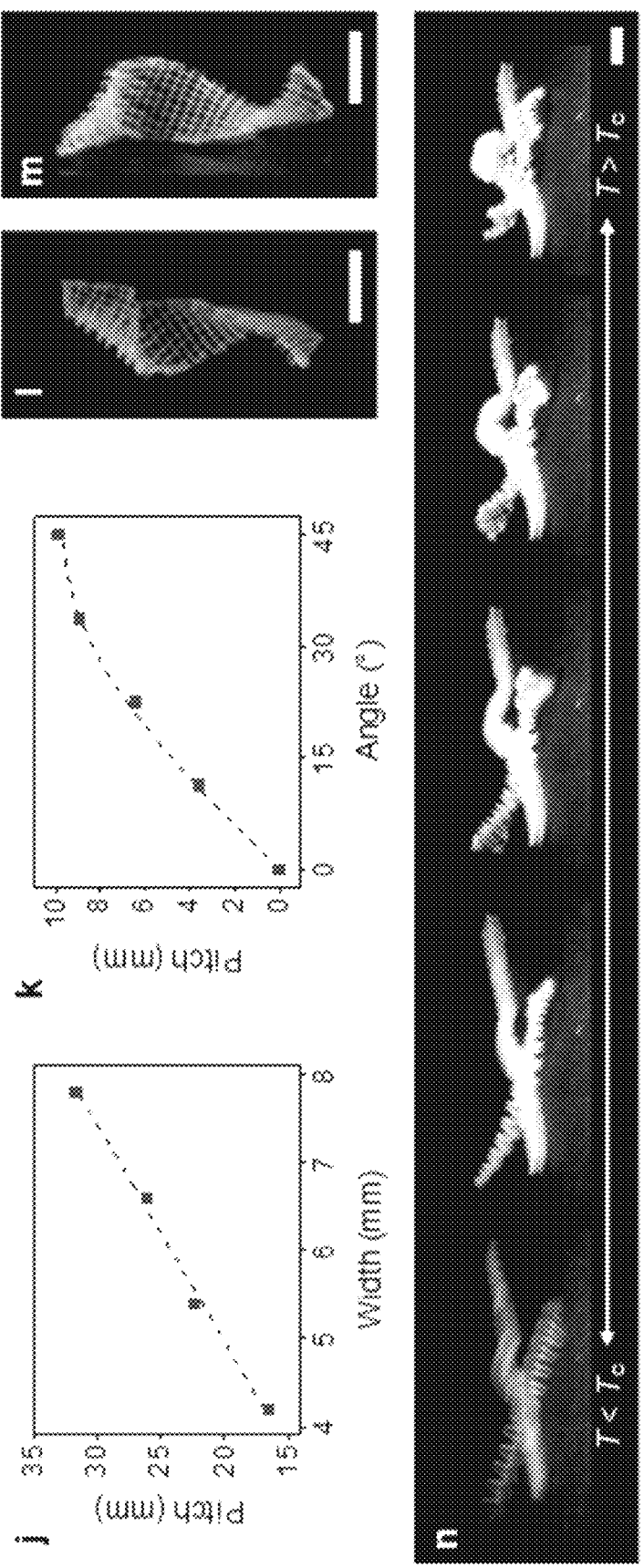

In addition to simple bending, the saddle-like shape change can be exploited to produce twisting motions (FIG. 4a-i). This can be considered analogous to biological organisms that generate twisting motions through the assembly of linear contractile elements in a bilayer configuration, such as heart tissues and Bauhinia seed pods. For example, the seed pod consists of two orthogonally oriented fibrous tissue layers at 45° with respect to the pod's long axis ($\theta = 45°$). When drying, the anisotropic shrinkage of the tissue layers in the orthogonal directions leads to the flat-to-helical transition, opening the pod. As observed in the seed pod, an orthogonally growing bilayer structure oriented at 45° with respect to its long axis ($\theta = 45°$) produces twisting motion (FIG. 4a). When it shrinks ($T > T_a$), the structure tends to bend along the perpendicular axes (±45° with respect to its longitudinal axis) in two opposite (upward and downward) directions (FIG. 4a). This behavior causes a metric incompatibility, inducing twisting motion. The metric of such a bilayer structure with $\theta = 45°$ can be obtained by rotating the metric for the structure with $\theta = 0°$ or 90° in Equation 3 by 45°:

$$b_r = \frac{3(\alpha^2 - \beta^2)}{4t} \begin{pmatrix} 0 & 1 \\ 1 & 0 \end{pmatrix}. \quad (5)$$

The metric $b_r$ (curvature tensor) with non-diagonal matrix elements in Equation 5 reflects pure twisting along the long axis.

F. Programmability of Motion

The programmability of twisting motion was next investigated. In the process of forming a helical twist, the width w of the bilayer structure plays a critical role. For example, the theoretical model for the seed pod suggests a transition from the bending-dominated regime (w<$w_c$, where $w_c$ is a critical width) to the stretching-dominated regime (w>$w_c$) with w, which yield cylindrical and twisted helices, respectively. Bilayer structures were printed with different w and characterized their twisting motions by monitoring the pitch p and radius r of the resulting helical twists at the shrunk state (FIG. 4b-e). p was found to increase with w (p~4w), while r=0, allowing us to structurally program twisting motions (FIG. 4j). These results also indicate that the twisting motion of the bilayer structures is in the bending-dominated regime (b~$b_r$), in which p increases with w but r=0.

To further investigate the possibility of programming twisting motions, the mechanism of how the orthogonally growing bilayer structure changes its motion from bending (θ=0°) to twisting (θ=45°). FIG. 4f-ii shows the equilibrium configurations of the structures with the same w but varying e from 0° to 45° at the shrunk state. As θ increases, the configurations transform from an arc shape (θ=0°; bending) to a cylindrical helix (θ=22.5°; hybrid bending and twisting) to a helical twist (θ=45°; twisting), which mimic various motions of plants, for example, those of pine cone scales, coiled tendrils of climbing plants, and Bauhinia seed pods, respectively. The pitch of the configurations increases with θ, whereas their radius decreases (FIG. 4f-i). This behavior agrees well with the theoretical prediction for the seed pod in the bending-dominated regime p=($2\pi/k_0$) sin 2θ (dashed line in FIG. 4k), where the curvature of the arc structure with θ=0° (FIG. 4f) is used as $k_0$ ($k_0$=0.65 mm$^{-1}$). The structures with θ of 90° to 45° induce the same motions as those with θ of 0° to 45°, whereas those with θ of 90° to 180° produce motions with reversed handedness (FIG. 4l-m; FIG. 14a-b). The examples shown in FIGS. 3 and 4 illustrate a variety of motions achievable by controlling the orientation and geometry of the simple bilayer structure with orthogonally oriented linear contractile elements.

G. Modularity of Structures

The modular nature of the approach disclosed herein, in combination with the flexibility of the disclosed 3D printing method, offers a versatile way to create multimodular 3D structures with complex motions. To demonstrate this capability, multimodular 3D structures were fabricated that consisted of multiple functional components (FIG. 4n). The structures show complex motions that combine linear contraction, bending, and twisting. As demonstrated in these examples, the modular approach could potentially enable programming of an unlimited number of motions into 3D structures beyond those of biological counterparts.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A gel-phase ink, wherein the gel-phase ink comprises a precursor solution and a fugitive carrier, wherein the precursor solution comprises (i) one or more crosslinkable monomers, one or more crosslinkable polymers, or a combination thereof, and (ii) optionally at least one crosslinker, one or more non-crosslinkable polymers, or a combination thereof, and wherein the fugitive carrier comprises a poloxamer in the amount of greater than 20 wt % to about 50 wt % of the gel-phase ink, wherein the fugitive carrier is a single poloxamer having the formula

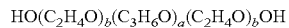

wherein a is from 50 to 70 and each b is from 50 to 150.

2. The gel-phase ink of claim 1, wherein the one or more crosslinkable monomers comprises 4-pentenoic acid, methacrylamide, vinylphenylboronic acid, acrylamide, N-isopropylmethacrylamide, butyl acrylate, N-vinyl-2-pyrrolidinone, N-hydroxymethylacrylamide, N-vinylacetamide, poly(ethylene glycol) methacrylate, methacrylated hyaluronic acid, or any combination thereof.

3. The gel-phase ink of claim 1, wherein the at least one crosslinker comprises two or more acryloyl groups, methacryloyl groups, or a combination thereof.

4. The gel-phase ink of claim 1, wherein the at least one crosslinker is a polyalkylene oxide glycol diacrylate or dimethacrylate.

5. The gel-phase ink of claim 1, wherein the at least one crosslinker comprises polyethylene glycol diacrylate (PEGDA), N,N-methylenebisacrylamide (BIS), or a combination thereof.

6. The gel-phase ink of claim 1, wherein the precursor solution comprises dimethylacrylamide (DMA) and polyethylene glycol diacrylate (PEGDA).

7. The gel-phase ink of claim 6, wherein the gel-phase ink comprises from about 5 wt % to about 15 wt % of the gel-phase ink DMA and from about 0.1 wt % to about 2 wt % of the gel-phase ink PEGDA.

8. The gel-phase ink of claim 1, wherein the precursor solution comprises N-isopropylmethacrylamide (NIPAM) and N,N-methylenebisacrylamide (BIS).

9. The gel-phase ink of claim 8, wherein the gel-phase ink comprises from about 5 wt % to about 15 wt % of the gel-phase ink NIPAM and from about 0.1 wt % to about 2 wt % of the gel-phase ink BIS.

10. The gel-phase ink of claim 1, wherein the fugitive carrier has a shear modulus of from about 10 kPa to about 50 kPa.

11. The gel-phase ink of claim 1, wherein the fugitive carrier comprises a poloxamer from about 20 to about 30 wt % of the gel-phase ink.

12. The gel-phase ink of claim 1, further comprising an initiator.

13. The gel-phase ink of claim 12, wherein the initiator comprises a type I photoinitiator, and wherein the type I photoinitiator comprises 2,2-diethoxyacetophenone, 2-benzyl-2-(dimethylamino)-4'-morpholinobutyrophenone, 4'-tert-butyl-2',6'-dimethylacetophenone, 2,2-dimethoxy-2-phenylacetophenone, a diphenyl (2,4,6-trimethylbenzoyl) phosphine oxide/2-hydroxy-2-methylpropiophenone blend, 4'-ethoxyacetophenone, 3'-hydroxyacetophenone, 4'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, lithium phenyl-2,4,6-trimethylbenzoylphosphinate (LAP), or a combination thereof.

14. The gel-phase ink of claim 1, further comprising biological cells.

15. The gel-phase ink of claim 1, wherein the one or more crosslinkable monomers comprises methacrylated hyaluronic acid.

* * * * *